US009017976B2

(12) United States Patent
Gong et al.

(10) Patent No.: US 9,017,976 B2
(45) Date of Patent: Apr. 28, 2015

(54) ENGINEERING MICROBES FOR EFFICIENT PRODUCTION OF CHEMICALS

(75) Inventors: Wei Gong, Woburn, MA (US); Sudhanshu Dole, North Andover, MA (US); Tammy Grabar, Reading, MA (US); Andrew Christopher Collard, Sommerville, MA (US); Janice G. Pero, Lexington, MA (US); R. Rogers Yocum, Lexington, MA (US)

(73) Assignee: Myriant Corporation, Quincy, MA (US)

( * ) Notice: Subject to any disclaimer, the term of this patent is extended or adjusted under 35 U.S.C. 154(b) by 3 days.

(21) Appl. No.: 13/503,999

(22) PCT Filed: Nov. 17, 2010

(86) PCT No.: PCT/US2010/057119
§ 371 (c)(1),
(2), (4) Date: Apr. 25, 2012

(87) PCT Pub. No.: WO2011/063055
PCT Pub. Date: May 26, 2011

(65) Prior Publication Data
US 2012/0220000 A1    Aug. 30, 2012

Related U.S. Application Data

(60) Provisional application No. 61/281,481, filed on Nov. 18, 2009.

(51) Int. Cl.
*B29C 70/04* (2006.01)
*C12N 15/74* (2006.01)
*C12N 1/00* (2006.01)
*A61B 6/04* (2006.01)
*B29L 31/00* (2006.01)

(52) U.S. Cl.
CPC ............... *A61B 6/0442* (2013.01); *B29C 70/04* (2013.01); *B29L 2031/753* (2013.01)

(58) Field of Classification Search
CPC ............ C12N 1/00; C12N 9/00; C12N 15/00; C12N 15/74; C12P 7/00; C12P 39/00; C12P 2203/00; C12P 7/46; A61B 6/0442
USPC .......................................... 435/145, 243, 471
See application file for complete search history.

(56) References Cited

U.S. PATENT DOCUMENTS

| 6,455,284 | B1 | 9/2002 | Gokarn et al. |
| 6,962,794 | B2 | 11/2005 | Valle et al. |
| 6,989,265 | B2 | 1/2006 | Blattner et al. |
| 7,223,567 | B2 | 5/2007 | Ka-Yiu et al. |
| 7,229,794 | B2 | 6/2007 | Park et al. |
| 7,303,906 | B2 | 12/2007 | Blattner et al. |
| 7,371,558 | B2 | 5/2008 | Cervin et al. |
| 7,524,660 | B2 | 4/2009 | Caimi et al. |
| 7,629,162 | B2 | 12/2009 | Zhou et al. |
| 2004/0146966 | A1 | 7/2004 | Cheng et al. |
| 2004/0214294 | A1 | 10/2004 | Rieping |
| 2005/0176114 | A1 | 8/2005 | Park et al. |
| 2005/0181488 | A1 | 8/2005 | Akhverdian et al. |
| 2005/0221455 | A1 | 10/2005 | McFarlan et al. |
| 2006/0073577 | A1 | 4/2006 | Ka-Yiu et al. |
| 2007/0111294 | A1 | 5/2007 | Burgard et al. |
| 2008/0009041 | A1 | 1/2008 | Mizoguchi et al. |
| 2008/0176302 | A1 | 7/2008 | Cervin et al. |
| 2008/0293100 | A1 | 11/2008 | Wendisch et al. |
| 2009/0047719 | A1 | 2/2009 | Burgard et al. |
| 2009/0075333 | A1 | 3/2009 | Campbell et al. |
| 2009/0075352 | A1 | 3/2009 | Lee et al. |
| 2009/0221055 | A1 | 9/2009 | Kadoya et al. |
| 2009/0325243 | A1 | 12/2009 | Park et al. |
| 2010/0143997 | A1 | 6/2010 | Buelter et al. |
| 2010/0248311 | A1 | 9/2010 | Figge |

(Continued)

FOREIGN PATENT DOCUMENTS

EP    2241630 A1    10/2010
WO    2008115958 A2    9/2008

(Continued)

OTHER PUBLICATIONS

Altaras, N. E. et al. "Metabolic engineering of a 1,2-propanediol pathway in *Escherichia coli*." Applied Environmental Microbiology, 1999, pp. 1180-1185, vol. 65.

Andersson, C. et al. "Effect of different carbon sources on the production of succinic acid using metabolically engineered *Escherichia coli*." Biotechnology Progress, 2007, pp. 381-388, vol. 23.

Babitzke, P. and Romeo, T. "CsrB sRNA family; sequestration of RNA-binding regulatory proteins." Current Opinion in Microbiology, 2007, pp. 156-163, vol. 10.

Causey, T.B. et al. "Engineering *Escherichia coli* for efficient conversion of glucose to pyruvate." Proceedings of National Academy of Sciences USA, 2004, pp. 2235-2240, vol. 101.

(Continued)

*Primary Examiner* — Suzanne M Noakes
*Assistant Examiner* — Gerard Lacourciere
(74) *Attorney, Agent, or Firm* — Ramasamy Mannan

(57) ABSTRACT

This present invention relates to production of chemicals from microorganisms that have been genetically engineered and metabolically evolved. Improvements in chemical production have been established, and particular mutations that lead to those improvements have been identified. Specific examples are given in the identification of mutations that occurred during the metabolic evolution of a bacterial strain genetically engineered to produce succinic acid. This present invention also provides a method for evaluating the industrial applicability of mutations that were selected during the metabolic evolution for increased succinic acid production. This present invention further provides microorganisms engineered to have mutations that are selected during metabolic evolution and contribute to improved production of succinic acid, other organic acids and other chemicals of commercial interest.

17 Claims, No Drawings

(56) References Cited

U.S. PATENT DOCUMENTS

2010/0261239 A1  10/2010  Soucaille et al.
2010/0279369 A1  11/2010  Soucaille et al.

FOREIGN PATENT DOCUMENTS

WO   WO 2009/011974   *  1/2009
WO      2010115067 A2   10/2010

OTHER PUBLICATIONS

Cronan, J. and Laporte, D. "Tricarboxylic acid cycle and glyoxylate bypass" in "*Escherichia Coli* and *Salmonella*-Cellular and Molecular Biology." editors Neidhardt, F. et al.1996, pp. 206-216, vol. 1, ASM Press, Washington, DC., USA.
Datsenko, K. A. and Wanner, B. L. "One-step inactivation of chromosomal genes in *Escherichia coli* K-12 using PCR products." Proceedings of National Academy of Science USA, 2000, pp. 6640-6645, vol. 97.
Fritsch, P.S. et al. "Role of RNA Polymerase alpha subunit in MetR-dependent activation of metE and metH: Important residues in the C-terminal domain and orientation requirements within RNA polymerase" Journal of Bacteriology, 2000, pp. 5539-5550, vol. 182.
Holcroft, C.C. and Egan S. M. Journal of Bacteriology, 2000, pp. 3529-3535, vol. 182.
Ikeda, M. et al. "A genome-based approach to create a minimally mutated *Corynebacterium glutamicum* strain for efficient L-lysine production." Journal of Industrial Microbiology and Biotechnology, 2006, pp. 610-615, vol. 33.
Jantama, K. et al. "Combining metabolic engineering and metabolic evolutions to develop nonrecombinant strains of *Escherichia coli* C that produce succinate and malate." Biotechnology and Bioengineering, 2008, pp. 1140-1153, vol. 99.
Jantama, K. et al."Eliminating side products and increasing succinate yields in engineered strains of *Escherichia coli* C." Biotechnology and Bioengineering, 2008, pp. 881-893, vol. 101.
Kurzrock, T. and Weuster-Botz, D. "Recovery of succinic acid from fermentation broth." Biotechnology Letters, 2009, pp. 331-339, vol. 32.
Kang, Y. et al. "Systematic mutagenesis of the *Escherichia coli* genome." Journal of Bacteriology, 2004, pp. 4921-4930, vol. 186.
Kolisnychenko, V. et al. "Engineering a reduced *Escherichia coli* genome." Genome Resesarch, 2009, pp. 640-647, vol. 12.
Lee, S.J. et al. "Metabolic Engineering of *Escherichia coli* for enhanced production of succinic acid, based on genome comparison and in silico gene knockout stimulation." Applied and Environmental Microbiology, 2005, pp. 7880-7887, vol. 71.
Lee, S. Y. et al. "Systems biotechnology for strain improvement." Trends in Biotechnology, 2005, pp. 349-358, vol. 23.
Lee, S. Y. et al. "From genome sequence to integrated bioprocess for succinic acid production by *Mannheimia succiniproducens*." Applied Microbiology and Biotechnology, 2008, pp. 11-22, vol. 79.
Lu, S. et al. "pH and base counterion affect succinate production in dual-phase *Escherichia coli* fermentations." Journal of Industrial Microbiology and Biotechnology,2009, pp. 1101-1109, vol. 36.
Martinez, A. et al. "Low salt medium for lactate and ethanol production by recombinant *Escherichia coli*." Biotechnology Letters, 2007, pp. 397-404, vol. 29.

Millard, C. S., et al. "Enhanced production of succinic acid by overexpression of phosphoenolpyruvate carboxyalse in *Escherichia coli*." Applied and Environmental Microbiology, 1996, pp. 1808-1810, vol. 62.
Pernesig, A. K. et al. "The *Escherichia coli* BarA-UvrY two component system is needed for efficient switching between glycolytic and gluconeogenic carbon sources." Journal of Bacteriology, 2003, pp. 843-853, vol. 185.
Ponce, E. et al "Cloning of the two pyruvate kinase isoenzymes structural genes from *Escherichia coli*: the relative roles of these enzymes in pyruvate biosynthesis." Journal of Bacteriology, 1995, pp. 5719-5722, vol. 177.
Posfai, G. et al. "Emergent properties of reduced-genome *Escherichia coli*." Science, 2006, pp. 1044-1046, vol. 312.
Saier, M. H. Jr. and and Ramseier, T. M. "The catabolite repressor/activator (Cra) protein of enteric bacteria." Journal of Bacteriology, 1996, pp. 3411-3417, vol. 178.
Sanchez, A.M. et al. "Novel pathway engineering design of the anaerobic central metabolic pathway in *Escherichia coli* to increase succinate yield and productivity." Metabolic Engineering, 2005, pp. 229-239, vol. 7.
Siebold, C. et al. "A mechanism of covalent substrate binding in the x-ray structure of subunit K of the *Escherichia coli* dihydroxyacetone kinase." Proceedings of National Academy of Sciences, USA, 2003, pp. 8188-8192, vol. 100.
Silhavy, T. et al. "Procedure 10—Preparation of Pivir Lysates" in "Experiments With Gene Fusions." 1984, pp. 107-112, Cold Spring Harbor Laboratory Press, Cold Spring Harbor, NY.
Subedi K. P. et al. "Role of gldA in dihydroxyacetone and methylglyoxal metabolism of *Escherichia coli* K12." FEMS Microbiology Letters, 2007, pp. 180-187, vol. 279.
Suzuki, K. et al. "Regulatory circuitary of the CsrA/CsrB and BarA/UvrY systems of *Escherichia coli*." Journal of Bacteriology, 2002, pp. 5130-5140, vol. 184.
Sivagamisundaram, C. et al. "Global effects of inactivation of the pyruvate kinase gene in the *Mycobacterium tuberculosis* complex." Journal of Bacteriology, 2009, pp. 7545-7553, vol. 191.
Truniger, V. and Boos, W. "Mapping and cloning of gldA, the structural gene of the *Escherichia coli* glycerol dehydrogenase." Journal of Bacteriology, 1994, pp. 1796-1800, vol. 176.
Vemuri, G. N. et al. "Effects of growth mode and pyruvate carboxylase on succinic acid production by metabolically engineered strains of *Escherichia coli*." Applied and Environmental Microbiology, 2002, pp. 1715-1727, vol. 68.
Wang, Q. et al. "Genome-scale in silico aided metabolic analysis and flux comparisons of *Escherichia coli* to improve succinate production." Applied Microbiology and Biotechnology, 2006, pp. 887-894, vol. 73.
Weickert, M. J. and Adhya, S. "Control of transcription of Gal Repressor and isorepressor genes in *Escherichia coli*." Journal of Bacteriology,1993, pp. 251-258, vol. 175.
Zhang, X. et al. "Metaboli evolution of energy-conserving pathways for succinate production in *Escherichia coli*." Proceedings of National Academy of Sciences USA, 2009, pp. 20180-20185, vol. 106.
Zhang , X. et al. "Re-engineering *Escherichia coli* for succinate production in mineral salts medium." Applied and Environmental Microbiology, 2009, pp. 7807-7813, vol. 75.

\* cited by examiner

SEQUENCE LISTING

```
<160> NUMBER OF SEQ ID NOS: 39

<210> SEQ ID NO 1
<211> LENGTH: 1445
<212> TYPE: DNA
<213> ORGANISM: Escherchia coli KJ122
<220> FEATURE:
<221> NAME/KEY: CDS/pykA
<222> LOCATION: (1)..(1445)
<223> OTHER INFORMATION: Frameshift mutation; insertion of GC after base
      1023

<400> SEQUENCE: 1
atgtccagaa ggcttcgcag aacaaaaatc gttaccacgt taggcccagc aacagatcgc      60
gataataatc ttgaaaaagt tatcgcggcg ggtgccaacg ttgtacgtat gaacttttct     120
cacggctcgc ctgaagatca caaatgcgc gcggataaag ttcgtgagat tgccgcaaaa      180 ctgggcgtc atgtggctat tctgggtgac ctccaggggc ccaaaatccg tgtatccacc      240
tttaaagaag gcaaagtttt cctcaatatt ggggataaat tcctgctcga cgccaacctg     300
ggtaaaggtg aaggcgacaa agaaaaagtc ggtatcgact acaaaggcct gcctgctgac     360
gtcgtgcctg gtgacatcct gctgctggac gatggtcgcg tccagttaaa agtactggaa     420
gttcagggca tgaaagtgtt caccgaagtc accgtcggtg gtccctctc caacaataaa      480 ggtatcaaca aacttggcgg cggtttgtcg gctgaagcgc tgaccgaaaa agacaaagca     540
gacattaaga ctgcggcgtt gattggcgta gattacctgg ctgtctcctt cccacgctgt     600
ggcgaagatc tgaactatgc ccgtcgcctg gcacgcgatg caggatgtga tgcgaaaatt     660
gttgccaagg ttgaacgtgc ggaagccgtt tgcagccagg atgcaatgga tgacatcatc     720
ctcgcctctg acgtggtaat ggttgcacgt ggcgacctcg gtgtggaaat tggcgacccg     780
gaactggtcg gcattcagaa agcgttgatc cgtcgtgcgc gtcagctaaa ccgagcggta     840
atcacggcga cccagatgat ggagtcaatg attactaacc cgatgccgac gcgtgcagaa     900
gtcatggacg tagcaaacgc cgttctggat ggtactgacg ctgtgatgct gtctgcagaa     960
actgccgctg ggcagtatcc gtcagaaacc gttgcagcca tggcgcgcgt ttgcctgggt    1020
gcgcggaaaa aatcccgagc atcaacgttt ctaaacaccg tctggacgtt cagttcgaca    1080
atgtggaaga agctattgcc atgtcagcaa tgtacgcagc taaccacctg aaaggcgtta    1140
cggcgatcat caccatgacc gaatcgggtc gtaccgcgct gatgacctcc cgtatcagct    1200
ctggtctgcc aattttcgcc atgtcgcgcc atgaacgtac gctgaacctg actgctctct    1260
atcgtggcgt tacgccggtg cactttgata gcgctaatga cggcgtagca gctgccagcg    1320
aagcggttaa tctgctgcgc gataaaggtt acttgatgtc tggtgacctg gtgattgtca    1380
cccagggcga cgtgatgagt accgtggggtt ctactaatac cacgcgtatt ttaacggtag    1440
agtaa                                                                  1445

<210> SEQ ID NO 2
```

```
<211> LENGTH: 1042
<212> TYPE: DNA
<213> ORGANISM: Escherchia coli KJ122
<220> FEATURE:
<221> NAME/KEY: CDS/galS
<222> LOCATION: (1)..(1042)
<223> OTHER INFORMATION: Frameshift mutation, insertion of A after base
      246

<400> SEQUENCE: 2
atgatcacca ttcgtgatgt agcgcgtcag gctggcgtct ctgtggcaac ggtttcccgg     60
gtgctcaata acagcacgct ggtcagtgcc gacacgcgtg aagcagtaat gaaagccgtg    120
agtgagctgg attatcggcc aaacgccaat gcccaggcgc tggcaactca ggttagcgac    180
accattggcg tggtggtgat ggacgtttct gatgcgtttt tcggcgcgct ggtaaaagcg    240
gtggatacta gtcgctcagc agcatcagaa atacgtgcta atcggcaata gctatcatga    300
agcggaaaaa gagcgtcacg ccattgaggt gttaattcgc cagcgttgta atgcgttgat    360
tgttcactca aaagcattga gtgacgatga actggcgcaa tttatggata acattcccgg    420
tatggtgtta atcaaccgcg ttgtgccggg gtacgcccat cgttgcgttt gcctggataa    480
tctcagcggt gcccgaatgg cgacgcgcat gttgctgaat aacggtcatc aacgtattgg    540
ttatctttct tccagtcacg gcattgaaga tgacgccatg cgtaaagcag gctggatgag    600
tgcgttgaaa gagcaggata ttattccgcc ggaaagctgg attggcactg gtacgccgga    660
catgccgggc ggtgaggcgg cgatggttga actgctgggg cgcaatctac aacttaccgc    720
tgtatttgct tataacgaca atatggccgc tggcgcactg acagcattaa agataaatgg    780
cattgcgatt ccgttacatc tctcaatcat cggtttcgat gatattccca tcgcccgtta    840
caccgacccg caattaacga ccgtgcgtta tcccattgct tcaatggcta aattagccac    900
cgaactggcc ttgcagggggg cagcaggcaa tattgatcct cgtgccagcc actgttttat    960
gccgacgtta gtgcgtcgcc attctgtcgc aacgcgccag aatgcggcgg cgatcactaa   1020
ctcaacaaat caggcgatgt aa                                            1042

<210> SEQ ID NO 3
<211> LENGTH: 906
<212> TYPE: DNA
<213> ORGANISM: Escherchia coli KJ122
<220> FEATURE:
<221> NAME/KEY: misc_feature
<222> LOCATION: (448)..(449)
<223> OTHER INFORMATION: 48 kbp deletion between bases 448 and 449
      removes ydcI, ydcL, ydcO, ydcV and many other genes.

<400> SEQUENCE: 3
cagtcggtaa cctcgcgcat acagccgggc agtgacgtca tcgtctgcgc ggaaatggac     60
gaacagtggg gctacgtcgg tgctaaatca cgtcagcgct ggctgttttta cgcgtatgac    120 aggatacgga ggacagttgt ggcgcacgtt ttcggtgaac gcactctggc cacactggag    180
cgtcttctga gcctgctgtc ggcctttgag gtcgtggtat ggatgacgga tggctggccg    240
ctgtatgaat cacgcctgaa gggaaagctg cacgttatca gcaagcgtta cactcagcgc    300
attgagcgac ataatctgaa tctgagacaa catctggcaa ggctgggacg gaagtcgctg    360
tcgttctcaa aatcggtgga gctgcatgac aaggtcatcg gcattatctt gaacataaaa    420
cactatcagt aagttggagt cactaccctg aattcctgaa tttttgtcct taccgtttta    480
gaattaataa aaaaccccggc gctaaatgct taccgggttt tagatttatc aggcaaatag    540
cagggttaac cgctaatctg ctccatcgcc tgcaaaatac gcttatctga aatcggataa    600
```

```
ggcgtaccaa gttgttgagc gaagtaacta acgcgcagct cttctatcat ccaacggatc      660
tctttcacgt cttcatcctc acgacgtgca ggcggcagtt tgttgatcca ttgctgccac      720
gcctgctgga cgttttcgac tttcagcatc tgagcacggt cgcgatgtgg atcaaccgcc      780
agttttccca gtcgtttttc aatcgcctgc aaatatcgca gcgtgtcgcc cagccgtttg      840
aagccgttac cagtgacaaa accgcgatat accaacccgc ccatctgcgc tttaatgtca      900
gaaagc                                                                 906

<210> SEQ ID NO 4
<211> LENGTH: 990
<212> TYPE: DNA
<213> ORGANISM: Escherchia coli KJ122
<220> FEATURE:
<221> NAME/KEY: CDS/rpoA
<222> LOCATION: (1)..(990)
<223> OTHER INFORMATION: missense mutation c965T; p322L mutation

<400> SEQUENCE: 4
atgcagggtt ctgtgacaga gtttctaaaa ccgcgcctgg ttgatatcga gcaagtgagt       60
tcgacgcacg ccaaggtgac ccttgagcct ttagagcgtg ctttggcca tactctgggt      120 aacgcactgc gccgtattct gctctcatcg atgccgggtt gcgcggtgac cgaggttgag      180
attgatggtg tactacatga gtacagcacc aaagaaggcg ttcaggaaga tatcctggaa      240
atcctgctca acctgaaagg gctggcggtg agagttcagg caaagatga agttattctt      300 accttgaata aatctggcat tggccctgtg actgcagccg atatcaccca cgacggtgat      360
gtcgaaatcg tcaagccgca gcacgtgatc tgccacctga ccgatgagaa cgcgtctatt      420
agcatgcgta tcaaagttca gcgcggtcgt ggttatgtgc cggcttctac ccgaattcat      480
tcggaagaag atgagcgccc aatcggccgt ctgctggtcg acgcatgcta cagccctgtg      540
gagcgtattg cctacaatgt tgaagcagcg cgtgtagaac agcgtaccga cctggacaag      600
ctggtcatcg aaatggaaac caacggcaca atcgatcctg aagaggcgat tcgtcgtgcg      660
gcaaccattc tggctgaaca actgaaagct ttcgttgact acgtgatgt acgtcagcct      720 gaagtgaaag aagagaaacc agagttcgat ccgatcctgc tgcgcccgt tgacgatctg      780 gaattgactg tccgctctgc taactgcctt aaagcagaag ctatccacta tatcggtgat      840
ctggtacagc gtaccgaggt tgagctcctt aaaacgccta accttggtaa aaaatctctt      900
actgagatta agacgtgct ggcttcccgt ggactgtctc tgggcatgcg cctggaaaac      960
tggctaccgg caagcatcgc tgacgagtaa                                       990

<210> SEQ ID NO 5
<211> LENGTH: 4224
<212> TYPE: DNA
<213> ORGANISM: Escherchia coli KJ122
<220> FEATURE:
<221> NAME/KEY: CDS/rpoC
<222> LOCATION: (1)..(4224)
<223> OTHER INFORMATION: missense mutation G2441A; M747I mutation; gtg
      is the start codon

<400> SEQUENCE: 5
gtgaaagatt tattaaagtt tctgaaagcg cagactaaaa ccgaagagtt tgatgcgatc       60
aaaattgctc tggcttcgcc agacatgatc cgttcatggt ctttcggtga agttaaaaag      120
ccggaaacca tcaactaccg tacgttcaaa ccagaacgtg acggccttt ctgcgcccgt      180 atctttgggc cggtaaaaga ttacgagtgc ctgtgcggta agtacaagcg cctgaaacac      240
```

-continued

| | | | | |
|---|---|---|---|---|
| cgtggcgtca | tctgtgagaa | gtgcggcgtt | gaagtgaccc | agactaaagt | acgccgtgag | 300 |
| cgtatgggcc | acatcgaact | ggcttccccg | actgcgcaca | tctggttcct | gaaatcgctg | 360 |
| ccgtcccgta | tcggtctgct | gctcgatatg | ccgctgcgcg | atatcgaacg | cgtactgtac | 420 |
| tttgaatcct | atgtggttat | cgaaggcggt | atgaccaacc | tggaacgtca | gcagatcctg | 480 |
| actgaagagc | agtatctgga | cgcgctggaa | gagttcggtg | acgaattcga | cgcgaagatg | 540 |
| ggggcggaag | caatccaggc | tctgctgaag | agcatggatc | tggagcaaga | gtgcgaacag | 600 |
| ctgcgtgaag | agctgaacga | aaccaactcc | gaaaccaagc | gtaaaaagct | gaccaagcgt | 660 |
| atcaaactgc | tggaagcgtt | cgttcagtct | ggtaacaaac | agagtggat | gatcctgacc | 720 |
| gttctgccgg | tactgccgcc | agatctgcgt | ccgctggttc | cgctggatgg | tggtcgtttc | 780 |
| gcgacttctg | acctgaacga | tctgtatcgt | cgcgtcatta | accgtaacaa | ccgtctgaaa | 840 |
| cgtctgctgg | atctggctgc | gccggacatc | atcgtacgta | acgaaaaacg | tatgctgcag | 900 |
| gaagcggtag | acgccctgct | ggataacggt | cgtcgcggtc | gtgcgatcac | cggttctaac | 960 |
| aagcgtcctc | tgaaatcttt | ggccgacatg | atcaaaggta | aacagggtcg | tttccgtcag | 1020 |
| aacctgctcg | gtaagcgtgt | tgactactcc | ggtcgttctg | taatcaccgt | aggtccatac | 1080 |
| ctgcgtctgc | atcagtgcgg | tctgccgaag | aaaatggcac | tggagctgtt | caaaccgttc | 1140 |
| atctacggca | agctggaact | gcgtggtctt | gctaccacca | ttaaagctgc | gaagaaaatg | 1200 |
| gttgagcgcg | aagaagctgt | cgtttgggat | atcctggacg | aagttatccg | cgaacacccg | 1260 |
| gtactgctga | accgtgcacc | gactctgcac | cgtctgggta | tccaggcatt | tgaaccggta | 1320 |
| ctgatcgaag | gtaaagctat | ccagctgcac | ccgctggttt | gtcggcata | taacgccgac | 1380 |
| ttcgatggtg | accagatggc | tgttcacgta | ccgctgacgc | tggaagccca | gctggaagcg | 1440 |
| cgtgcgctga | tgatgtctac | caacaacatc | ctgtccccgg | cgaacggcga | accaatcatc | 1500 |
| gttccgtctc | aggacgttgt | actgggtctg | tactacatga | cccgtgactg | tgttaacgcc | 1560 |
| aaaggcgaag | gcatggtgct | gactggcccg | aaagaagcag | aacgtctgta | tcgctctggt | 1620 |
| ctggcttctc | tgcatgcgcg | cgttaaagtg | cgtatcaccg | agtatgaaaa | agatgctaac | 1680 |
| ggtgaattag | tagcgaaaac | cagcctgaaa | gacacgactg | ttggccgtgc | cattctgtgg | 1740 |
| atgattgtac | cgaaaggtct | gccttactcc | atcgtcaacc | aggcgctggg | taaaaaagca | 1800 |
| atctccaaaa | tgctgaacac | ctgctaccgc | attctcggtc | tgaaaccgac | cgttattttt | 1860 |
| gcggaccaga | tcatgtacac | cggcttcgcc | tatgcagcgc | gttctggtgc | atctgttggt | 1920 |
| atcgatgaca | tggtcatccc | ggagaagaaa | cacgaaatca | tctccgaggc | agaagcagaa | 1980 |
| gttgctgaaa | ttcaggagca | gttccagtct | ggtctggtaa | ctgcgggcga | acgctacaac | 2040 |
| aaagttatcg | atatctgggc | tgcggcgaac | gatcgtgtat | ccaaagcgat | gatggataac | 2100 |
| ctgcaaactg | aaaccgtgat | taaccgtgac | ggtcaggaag | agaagcaggt | tccttcaac | 2160 |
| agcatctaca | tgatggccga | ctccggtgcg | cgtggttctg | cggcacagat | tcgtcagctt | 2220 |
| gctggtatgc | gtggtctgat | agcgaagccg | gatggctcca | tcatcgaaac | gccaatcacc | 2280 |
| gcgaacttcc | gtgaaggtct | gaacgtactc | cagtacttca | tctccaccca | cggtgctcgt | 2340 |
| aaaggtctgc | cggataccgc | actgaaaact | gcgaactccg | ttacctgac | tcgtcgtctg | 2400 |
| gttgacgtgg | cgcaggacct | ggtggttacc | gaagacgatt | gtggtaccca | tgaaggtatc | 2460 |
| atgatgactc | cggttatcga | gggtggtgac | gttaaagagc | cgctgcgcga | tcgcgtactg | 2520 |
| ggtcgtgtaa | ctgctgaaga | cgttctgaag | ccgggtactg | ctgatatcct | cgttccgcgc | 2580 |

-continued

```
aacacgctgc tgcacgaaca gtggtgtgac ctgctggaag agaactctgt cgacgcggtt    2640
aaagtacgtt ctgttgtatc ttgtgacacc gactttggtg tatgtgcgca ctgctacggt    2700
cgtgacctgg cgcgtggcca tcatcaac aagggtgaag caatcggtgt tatcgcggca     2760
cagtccatcg gtgaaccggg tacacagctg accatgcgta cgttccacat cggtggtgcg    2820
gcatctcgtg cggctgctga atccagcatc aagtgaaaa acaaaggtag catcaagctc    2880
agcaacgtga gtcggttgt gaactccagc ggtaaactgg ttatcacttc ccgtaatact     2940
gaactgaaac tgatcgacga attcggtcgt actaaagaaa gctacaaagt accttacggt    3000
gcggtactgg cgaaaggcga tggcgaacag gttgctggcg cgaaaccgt tgcaaactgg     3060 gacccgcaca ccatgccggt tatcaccgaa gtaagcggtt ttgtacgctt tactgacatg    3120
atcgacggcc agaccattac gcgtcagacc gacgaactga ccggtctgtc ttcgctggtg    3180
gttctggatt ccgcagaacg taccgcaggt ggtaaagatc tgcgtccggc actgaaaatc    3240
gttgatgctc agggtaacga cgttctgatc ccaggtaccg atatgccagc gcagtacttc    3300
ctgccgggta aagcgattgt tcagctggaa gatggcgtac agatcagctc tggtgacacc    3360
ctggcgcgta ttccgcagga atccggcggt accaaggaca tcaccggtgg tctgccgcgc    3420
gttgcggacc tgttcgaagc acgtcgtccg aaagagccgg caatcctggc tgaaatcagc    3480
ggtatcgttt ccttcggtaa agaaaccaaa ggtaaacgtc gtctggttat caccccggta    3540
gacggtagcg atccgtacga agagatgatt ccgaaatggc gtcagctcaa cgtgttcgaa    3600
ggtgaacgtg tagaacgtgg tgacgtaatt tccgacggtc cggaagcgcc gcacgacatt    3660
ctgcgtctgc gtggtgttca tgctgttact cgttacatcg ttaacgaagt acaggacgta    3720
taccgtctgc agggcgttaa gattaacgat aaacacatcg aagttatcgt tcgtcagatg    3780
ctgcgtaaag ctaccatcgt taacgcgggt agctccgact tcctggaagg cgaacaggtt    3840
gaatactctc gcgtcaagat cgcaaaccgc gaactggaag cgaacggcaa agtgggtgca    3900
acttactccc gcgatctgct gggtatcacc aaagcgtctc tggcaaccga gtccttcatc    3960
tccgcggcat cgttccagga gaccactcgc gtgctgaccg aagcagccgt tgcgggcaaa    4020
cgcgacgaac tgcgcggcct gaaagagaac gttatcgtgg gtcgtctgat cccggcaggt    4080
accggttacg cgtaccacca ggatcgtatg cgtcgccgtg ctgcgggtga agctccggct    4140
gcaccgcagg tgactgcaga agacgcatct gccagcctgg cagaactgct gaacgcaggt    4200
ctgggcggtt ctgataacga gtaa                                          4224
```

<210> SEQ ID NO 6
<211> LENGTH: 1105
<212> TYPE: DNA
<213> ORGANISM: Escherchia coli KJ122
<220> FEATURE:
<221> NAME/KEY: CDS/gldA
<222> LOCATION: (1)..(1105)
<223> OTHER INFORMATION: frameshift mutation; insertion of C after base 717

<400> SEQUENCE: 6

```
atggaccgca ttattcaatc accgggtaaa tacatccagg cgctgatgt gattaatcgt      60 ctgggcgaat acctgaagcc gctggcagaa cgctggttag tggtgggtga caaatttgtt    120
ttaggttttg ctcaatccac tgtcgagaaa agctttaaag atgctggact ggtagtagaa    180
attgcgccgt ttgcggtga atgttcgcaa aatgagatcg accgtctgcg tggcatcgcg    240
gagactgcgc agtgtggcgc aattctcggt atcggtggcg gaaaaacccct cgatactgcc    300
```

| | |
|---|---|
| aaagcactgg cacatttcat gggtgttccg gtagcgatcg caccgactat cgcctctacc | 360 |
| gatgcaccgt gcagcgcatt gtctgttatc tacaccgatg agggtgagtt tgaccgctat | 420 |
| ctgctgttgc caaataaccc gaatatggtc attgtcgaca ccaaaatcgt cgctggcgca | 480 |
| cctgcacgtc tgttagcggc gggtatcggc gatgcgctgg caacctggtt tgaagcgcgt | 540 |
| gcctgctctc gtagcggcgc gaccaccatg gcgggcggca agtgcaccca ggctgcgctg | 600 |
| gcactggctg aactgtgcta caacaccctg ctggaagaag cgaaaaagc gatgcttgct | 660 |
| gccgaacagc atgtagtgac tccggcgctg agcgcgtga ttgaagcgaa cacctatctt | 720 |
| aagcggtgta ggctttgaaa gtggtggtct ggctgcggcg cacgcagtgc ataacggcct | 780 |
| gaccgctatc ccggacgcgc atcactatta tcacggtgaa aaagtggcat ttggtacgct | 840 |
| gacgcagctg gttctggaaa acgcaccggt tgaggaaatc gaaaccgtag ctgcacttag | 900 |
| ccatgcggta ggtttgccaa taactctcgc tcaactggat attaaagaag atgtcccggc | 960 |
| gaaaatgcga attgtggcag aagcggcatg tgcagaaggt gaaaccatcc acaacatgcc | 1020 |
| tggcggcgcg acgccagatc aggtttacgc cgctctgctg gtagccgacc agtacggtca | 1080 |
| gcgtttcctg caagagtggg aataa | 1105 |

<210> SEQ ID NO 7
<211> LENGTH: 1417
<212> TYPE: DNA
<213> ORGANISM: Escherchia coli KJ122
<220> FEATURE:
<221> NAME/KEY: CDS/dhaM
<222> LOCATION: (1)..(1417)
<223> OTHER INFORMATION: frameshift mutation; deletion between bases
      1256 and 1266

<400> SEQUENCE: 7

| | |
|---|---|
| atggtaaacc tggtcatagt ttcacatagc agccgactgg gagaaggtgt cggtgaatta | 60 |
| gcccgtcaga tgttaatgag tgatagttgt aaaatcgcca ttgccgcggg aattgacgat | 120 |
| ccacaaaatc ccattggtac cgatgccgtc aaagtgatgg aggccatcga atctgttgct | 180 |
| gatgccgacc atgtgctggt catgatggat atgggtagcg cattattgag tgctgaaact | 240 |
| gcgctggaat tgctggctcc cgagatcgcc gcaaaagtac gtttgtgtgc tgcgccgttg | 300 |
| gtcgaaggta cactggcagc aacggtcagc gcggcctcgg gggcggatat cgacaaagtt | 360 |
| atctttgacg ccatgcatgc gctggaagcc aaacgtgaac aactgggttt accgtcctcc | 420 |
| gacactgaaa tctctgacac atgtcctgcg tacgatgaag aagcccgttc tctggcggtg | 480 |
| gtcataaaaa accgtaacgg cctgcatgta cgtccggcct cccggctggt ttataccta | 540 |
| tcgacattta atgccgatat gttgctggaa aaaacggca atgcgtcac accagagagt | 600 |
| attaaccaga ttgcgttact acaagttcgc tataacgata cgctgcgcct gattgcgaaa | 660 |
| gggccagaag ctgaagaggc actgatcgct ttccgtcagc tggctgaaga taactttggt | 720 |
| gaaacggagg aagtcgctcc acctactctg cgtcccgttc cgcctgtttc gggtaaagcc | 780 |
| ttttattatc aaccagtttt atgtacggta caggcaaaat caaccctgac cgtggaagaa | 840 |
| gaacaagatc gattacgcca ggctattgac ttcacgttat tagatctgat gacgttaaca | 900 |
| gcgaaagcag aagccagcgg gcttgacgat attgccgcaa tctttttctgg tcaccataca | 960 |
| ctgttagatg atccggaact gctggcggcg gcaagcgaac tccttcagca tgaacattgc | 1020 |
| acggcagaat atgcctggca gcaagttctt aaagaactta gccagcaata ccagcaactg | 1080 |
| gatgatgaat atctacaagc tcgctatatt gatgtggacg atcttctgca tcgcaccctg | 1140 |

-continued

| | |
|---|---|
| gtccacctga cccaaacgaa agaagaactc ccgcagttta actcgccaac tattctactg | 1200 |
| gcggagaaca tttatccttc cacagtactg caactggatc cggcggttgt aaaaggtatc | 1260 |
| tgcctgcgcc ggaagtccgg tatcccacag cgccctaatc gcccgtgaac tggggattgg | 1320 |
| ctggatttgc cagcagggtg agaaactgta tgcgatacaa ccagaagaaa cgctaacgct | 1380 |
| ggacgttaaa acgcaacgtt tcaaccgtca gggttaa | 1417 |

<210> SEQ ID NO 8
<211> LENGTH: 1767
<212> TYPE: DNA
<213> ORGANISM: Escherchia coli KJ122
<220> FEATURE:
<221> NAME/KEY: CDS/ftsI
<222> LOCATION: (1)..(1767)
<223> OTHER INFORMATION: missense mutation C619T; R206C

<400> SEQUENCE: 8

| | |
|---|---|
| atgaaagcag cggcgaaaac gcagaaacca aaacgtcagg aagaacatgc caactttatc | 60 |
| agttggcgtt ttgcgttgtt atgcggctgt attctcctgg cgctggcttt tctgctcgga | 120 |
| cgcgtagcgt ggttacaagt tatctccccg gatatgctgg tgaaagaggg cgacatgcgt | 180 |
| tctcttcgcg ttcagcaagt ttccacctcc cgcggcatga ttactgaccg ttctggtcgc | 240 |
| ccgttagcgg tgagcgtgcc ggtaaaagcg atttgggctg acccgaaaga agtgcatgac | 300 |
| gctggcggta tcagcgtcgg tgaccgctgg aaggcgctgg ctaacgcgct caatattccg | 360 |
| ctggatcagc tttcagcccg cattaacgcc aacccgaaag gcgctttat ttatctggcg | 420 |
| cgtcaggtga accctgacat ggcggactac atcaaaaaac tgaaactgcc ggggattcat | 480 |
| ctgcgtgaag agtctcgccg ttactatccg tccggcgaag tgactgctca cctcatcggc | 540 |
| tttactaacg tcgatagtca agggattgag ggcgttgaga gagtttcga taaatggctt | 600 |
| accgggcagc cgggtgagtg cattgtgcgt aaagaccgct atggtcgcgt aattgaagat | 660 |
| atttcttcta ctgacagcca ggcagcgcac aacctggcgc tgagtattga tgaacgcctg | 720 |
| caggcgctgg tttatcgcga actgaacaac gcggtggcct taacaaggc tgaatctggt | 780 |
| agcgccgtgc tggtggatgt caacaccggt gaagtgctgg cgatggctaa cagcccgtca | 840 |
| tacaacccta acaatctgag cggcacgccg aaagaggcga tgcgtaaccg taccatcacc | 900 |
| gacgtgtttg aaccgggctc aacggttaaa ccgatggtgg taatgaccgc gttgcaacgt | 960 |
| ggcgtggtgc gggaaaactc ggtactcaat accattcctt atcgaattaa cggccacgaa | 1020 |
| atcaaagacg tggcacgcta cagcgaatta accctgaccg gggtattaca gaagtcgagt | 1080 |
| aacgtcggtg tttccaagct ggcgttagcg atgccgtcct cagcgttagt agatacttac | 1140 |
| tcacgttttg gactgggaaa agcgaccaat ttggggttgg tcgagaacg cagtggctta | 1200 |
| tatcctcaaa acaacggtg gtctgacata gagagggcca ccttctcttt cggctacggg | 1260 |
| ctaatggtaa caccattaca gttagcgcga gtctacgcaa ctatcggcag ctacggcatt | 1320 |
| tatcgcccac tgtcgattac caaagttgac ccccggttc ccgtgaacg tgtcttcccg | 1380 |
| gaatccattg tccgcactgt ggtgcatatg atggaaagcg tggcgctacc aggcggcggc | 1440 |
| ggcgtgaagg cggcgattaa aggctatcgt atcgccatta aaaccggtac cgcgaaaaag | 1500 |
| gtcgggccgg acggtcgcta tcatcaataaa tatattgctt ataccgcagg cgttgcgcct | 1560 |
| gcgagtcagc cgcgcttcgc gctggttgtt gttatcaacg atccgcaggc gggtaaatac | 1620 |
| tacgcggccg ccgtttccgc gccggtcttt ggtgccatca tgggcggcgt attgcgtacc | 1680 |
| atgaacatcg agccggatgc gctgacaacg ggcgataaaa atgaatttgt gattaatcaa | 1740 |

-continued ggcgagggga caggtggcag atcgtaa                                              1767

<210> SEQ ID NO 9
<211> LENGTH: 77
<212> TYPE: DNA
<213> ORGANISM: Artificial Sequence
<220> FEATURE:
<223> OTHER INFORMATION: Synthetic PCR Primer BY60

<400> SEQUENCE: 9
caggaaacgc tgaccgtact ggtcggctac cagcagagcg gcgtaaacct gtgacggaag    60
atcacttcgc agaataa                                                    77

<210> SEQ ID NO 10
<211> LENGTH: 76
<212> TYPE: DNA
<213> ORGANISM: Artificial Sequence
<220> FEATURE:
<223> OTHER INFORMATION: Synthetic PCR Primer BY61

<400> SEQUENCE: 10
gtgagtttga ccgctatctg ctgttgccaa ataacccgaa tatggtcatt gaagcacttc    60
actgacaccc tcatca                                                    76

<210> SEQ ID NO 11
<211> LENGTH: 79
<212> TYPE: DNA
<213> ORGANISM: Artificial Sequence
<220> FEATURE:
<223> OTHER INFORMATION: Synthetic PCR Primer BY62

<400> SEQUENCE: 11
tctctggcgg tggtcataaa aaaccgtaac ggcctgcatg tacgtccggc gtgacggaag    60
atcacttcgc agaataaat                                                 79

<210> SEQ ID NO 12
<211> LENGTH: 76
<212> TYPE: DNA
<213> ORGANISM: Artificial Sequence
<220> FEATURE:
<223> OTHER INFORMATION: Synthetic PCR Primer BY63

<400> SEQUENCE: 12
aaccctgacg gttgaaacgt tgcgttttaa cgtccagcgt tagcgtttct gaagcacttc    60
actgacaccc tcatca                                                    76

<210> SEQ ID NO 13
<211> LENGTH: 28
<212> TYPE: DNA
<213> ORGANISM: Artificial Sequence
<220> FEATURE:
<223> OTHER INFORMATION: synthetic PCR Primer AC16

<400> SEQUENCE: 13
gcattgtctg ttatctacac cgatgagg                                        28

<210> SEQ ID NO 14
<211> LENGTH: 22
<212> TYPE: DNA
<213> ORGANISM: Artificial Sequence
<220> FEATURE:
<223> OTHER INFORMATION: Synthetic PCR Primer AC17

```
<400> SEQUENCE: 14
tcccactctt gcaggaaacg ct                                        22

<210> SEQ ID NO 15
<211> LENGTH: 24
<212> TYPE: DNA
<213> ORGANISM: Artificial Sequence
<220> FEATURE:
<223> OTHER INFORMATION: Synthetic PCR Primer AC33

<400> SEQUENCE: 15
gactgggaga aggtgtcggt gaat                                      24

<210> SEQ ID NO 16
<211> LENGTH: 29
<212> TYPE: DNA
<213> ORGANISM: Artificial Sequence
<220> FEATURE:
<223> OTHER INFORMATION: Synthetic PCR primer AC34

<400> SEQUENCE: 16
catcattaaa cagcggccct aataaaata                                 29

<210> SEQ ID NO 17
<211> LENGTH: 80
<212> TYPE: DNA
<213> ORGANISM: Artificial Sequence
<220> FEATURE:
<223> OTHER INFORMATION: Synthetic PCR Primer 91A

<400> SEQUENCE: 17
aaacgccaat gcccaggcgc tggcaactca ggttagcgac accattggcg tggtggtgat    60
ctagcgcatg catccattta                                               80

<210> SEQ ID NO 18
<211> LENGTH: 80
<212> TYPE: DNA
<213> ORGANISM: Artificial Sequence
<220> FEATURE:
<223> OTHER INFORMATION: Synthetic PCR Primer 91B

<400> SEQUENCE: 18
aatcaacgca ttacaacgct ggcgaattaa cacctcaatg gcgtgacgct cttttccgc     60 ggcgaagaac tccagcatga                                               80

<210> SEQ ID NO 19
<211> LENGTH: 20
<212> TYPE: DNA
<213> ORGANISM: Artificial Sequence
<220> FEATURE:
<223> OTHER INFORMATION: Synthetic PCR primer 90A

<400> SEQUENCE: 19
gaataacagc acgctggtca                                           20

<210> SEQ ID NO 20
<211> LENGTH: 20
<212> TYPE: DNA
<213> ORGANISM: Artificial Sequence
<220> FEATURE:
<223> OTHER INFORMATION: Synthetic PCR Primer 90B

<400> SEQUENCE: 20
tcaacgcact catccagcct                                           20
```

<210> SEQ ID NO 21
<211> LENGTH: 80
<212> TYPE: DNA
<213> ORGANISM: Artificial Sequence
<220> FEATURE:
<223> OTHER INFORMATION: Synthetic PCR Primer 60A

<400> SEQUENCE: 21
atgtccagaa ggcttcgcag aacaaaaatc gttaccacgt taggcccagc aacagatcgc    60
gacggaagat cacttcgcag                                                80

<210> SEQ ID NO 22
<211> LENGTH: 80
<212> TYPE: DNA
<213> ORGANISM: Artificial Sequence
<220> FEATURE:
<223> OTHER INFORMATION: Synthetic PCR Primer 60B

<400> SEQUENCE: 22
ttactctacc gttaaaatac gcgtggtatt agtagaaccc acggtactca tcacgtcgcc    60
aagaaataaa agaaaatgcc                                                80

<210> SEQ ID NO 23
<211> LENGTH: 20
<212> TYPE: DNA
<213> ORGANISM: Artificial Sequence
<220> FEATURE:
<223> OTHER INFORMATION: Synthetic PCR Primer 59A

<400> SEQUENCE: 23
tacatgtcca gaaggcttcg                                                20

<210> SEQ ID NO 24
<211> LENGTH: 20
<212> TYPE: DNA
<213> ORGANISM: Artificial Sequence
<220> FEATURE:
<223> OTHER INFORMATION: Synthetic PCR Primer 59B

<400> SEQUENCE: 24
catccggcaa cgtacttact                                                20

<210> SEQ ID NO 25
<211> LENGTH: 80
<212> TYPE: DNA
<213> ORGANISM: Artificial Sequence
<220> FEATURE:
<223> OTHER INFORMATION: Synthetic PCR Primer 75A

<400> SEQUENCE: 25
ccaggacgat ccttgcgctt tacccatcag cccgtataat cctccacccg gcgcgccatg    60
ctagcgcatg catccattta                                                80

<210> SEQ ID NO 26
<211> LENGTH: 81
<212> TYPE: DNA
<213> ORGANISM: Artificial Sequence
<220> FEATURE:
<223> OTHER INFORMATION: Synthetic PCR Primer 75B

<400> SEQUENCE: 26
ccgcgctttt ccgcaccttt tcgcagggaa aatgtacgac ctcacaccag tggaaccag    60 cggcgaagaa ctccagcatg a                                                  81

<210> SEQ ID NO 27
<211> LENGTH: 80
<212> TYPE: DNA
<213> ORGANISM: Artificial Sequence
<220> FEATURE:
<223> OTHER INFORMATION: Synthetic PCR Primer 76A

<400> SEQUENCE: 27
ccaggacgat ccttgcgctt tacccatcag cccgtataat cctccacccg gcgcgccatg     60
ccgattacac caaccacaac                                                 80

<210> SEQ ID NO 28
<211> LENGTH: 81
<212> TYPE: DNA
<213> ORGANISM: Artificial Sequence
<220> FEATURE:
<223> OTHER INFORMATION: Synthetic PCR Primer 76B

<400> SEQUENCE: 28
ccgcgctttt ccgcaccttt tcgcagggaa aatgtacgac ctcacaccag tggaaaccag     60
cggcgaattt catagctttc c                                               81

<210> SEQ ID NO 29
<211> LENGTH: 80
<212> TYPE: DNA
<213> ORGANISM: Artificial Sequence
<220> FEATURE:
<223> OTHER INFORMATION: Synthetic PCR Primer 60A

<400> SEQUENCE: 29
atgtccagaa ggcttcgcag aacaaaaatc gttaccacgt taggcccagc aacagatcgc     60
gacggaagat cacttcgcag                                                 80

<210> SEQ ID NO 30
<211> LENGTH: 80
<212> TYPE: DNA
<213> ORGANISM: Artificial Sequence
<220> FEATURE:
<223> OTHER INFORMATION: Synthetic PCR Primer 60B

<400> SEQUENCE: 30
ttactctacc gttaaaatac gcgtggtatt agtagaaccc acggtactca tcacgtcgcc     60
aagaaataaa agaaaatgcc                                                 80

<210> SEQ ID NO 31
<211> LENGTH: 80
<212> TYPE: DNA
<213> ORGANISM: Artificial Sequence
<220> FEATURE:
<223> OTHER INFORMATION: Synthetic PCR Primer 67A

<400> SEQUENCE: 31
ggctgggacg gaagtcgctg tcgttctcaa aatcggtgga gctgcatgac aaggtcatcg     60
gacggaagat cacttcgcag                                                 80

<210> SEQ ID NO 32
<211> LENGTH: 80
<212> TYPE: DNA
<213> ORGANISM: Artificial Sequence
<220> FEATURE:
<223> OTHER INFORMATION: Synthetic PCR Primer 67B

<400> SEQUENCE: 32

```
atggagcaga ttagcggtta accctgctat ttgcctgata aatctaaaac ccgtaagca      60
aagaaataaa agaaaatgcc                                                  80
```

<210> SEQ ID NO 33
<211> LENGTH: 7929
<212> TYPE: DNA
<213> ORGANISM: Escherichia coli
<220> FEATURE:
<221> NAME/KEY: misc_feature
<222> LOCATION: (1545)..(1545)
<223> OTHER INFORMATION: n is a, c, g, or t; Plasmid pLOI4151; plasmid
      template in PCR for cat-sacB cassette
<220> FEATURE:
<221> NAME/KEY: misc_feature
<222> LOCATION: (3474)..(3474)
<223> OTHER INFORMATION: n is a, c, g, or t; Plasmid pLOI4151; plasmid
      template in PCR for cat-sacB cassette
<220> FEATURE:
<221> NAME/KEY: misc_feature
<222> LOCATION: (3475)..(3475)
<223> OTHER INFORMATION: n is a, c, g, or t; Plasmid pLOI4151; plasmid
      template in PCR for cat-sacB cassette

<400> SEQUENCE: 33

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccaa gcttgcatgc ctgcaggtcg     420
actctagagg atccccgggt accgagctcg aattcccgcg cccgatgaat tgatccgaag     480
ttcctattct ctagaaagta taggaacttc gaattgtcga caagctagca tgtgacggaa     540
gatcacttcg cagaataaat aaatcctggt gtccctgttg ataccgggaa gccctgggcc     600
aacttttggc gaaaatgaga cgttgatcgg cacgtaagag gttccaactt tcaccataat     660
gaaataagat cactaccggg cgtattttt gagttatcga gattttcagg agctaaggaa     720
gctaaaatgg agaaaaaaat cactggatat accaccgttg atatatccca atggcatcgt     780
aaagaacatt tgaggcatt tcagtcagtt gctcaatgta cctataacca gaccgttcag     840
ctggatatta cggccttttt aaagaccgta agaaaaata agcacaagtt tatccggcc     900
tttattcaca ttcttgcccg cctgatgaat gctcatccgg aattccgtat ggcaatgaaa     960
gacggtgagc tggtgatatg ggatagtgtt caccttgtt acaccgtttt ccatgagcaa    1020
actgaaacgt ttcatcgct ctggagtgaa taccacgacg atttccggca gtttctacac    1080
atatattcgc aagatgtggc gtgttacggt gaaaacctgg cctattccc taaagggttt    1140
attgagaata tgttttttcgt ctcagccaat ccctgggtga gtttcaccag ttttgattta    1200
aacgtggcca atatggacaa cttcttcgcc cccgttttca ccatgggcaa atattatacg    1260
caaggcgaca aggtgctgat gccgctggcg attcaggttc atcatgccgt tgtgatggc    1320
ttccatgtcg gcagaatgct taatgaatta acagtactg cgatgagtg cagggcggg     1380
gcgtaattt tttaaggcag ttattggtgc ccttaaacgc ctggtgctac gcctgaataa    1440
gtgataataa gcggatgaat ggcagaaatt cgaaagcaaa ttcgacccgg tcgtcggttc    1500
```

```
agggcagggt cgttaaatag ccgcttatgt ctattgctgg tttantcggt acccggggat    1560
cgcggccgcg gaccggatcc catcacatat acctgccgtt cactattatt tagtgaaatg    1620
agatattatg atattttctg aattgtgatt aaaaaggcaa ctttatgccc atgcaacaga    1680
aactataaaa aatacagaga atgaaaagaa acagatagat tttttagttc tttaggcccg    1740
tagtctgcaa atccttttat gattttctat caaacaaaag aggaaaatag accagttgca    1800
atccaaacga gagtctaata gaatgaggtc gaaaagtaaa tcgcgcgggt ttgttactga    1860
taaagcaggc aagacctaaa atgtgtaaag ggcaaagtgt atactttggc gtcaccccctt   1920 acatatttta ggtctttttt tattgtgcgt aactaacttg ccatcttcaa acaggagggc    1980
tggaagaagc agaccgctaa cacagtacat aaaaaggag acatgaacga tgaacatcaa     2040
aaagtttgca aaacaagcaa cagtattaac ctttactacc gcactgctgg caggaggcgc    2100
aactcaagcg tttgcgaaag aaacgaacca aaagccatat aaggaaacat acggcatttc    2160
ccatattaca cgccatgata tgctgcaaat ccctgaacag caaaaaaatg aaaaatatca    2220
agttcctgaa ttcgattcgt ccacaattaa aaatatctct tctgcaaaag gcctggacgt    2280
ttgggacagc tggccattac aaaacgctga cggcactgtc gcaaactatc acggctacca    2340
catcgtcttt gcattagccg gagatcctaa aaatgcggat gacacatcga tttacatgtt    2400
ctatcaaaaa gtcggcgaaa cttctattga cagctggaaa aacgctggcc gcgtctttaa    2460
agacagcgac aaattcgatg caaatgattc tatcctaaaa gaccaaacac aagaatggtc    2520
aggttcagcc acatttacat ctgacggaaa aatccgttta ttctacactg atttctccgg    2580
taaacattac ggcaaacaaa cactgacaac tgcacaagtt aacgtatcag catcagacag    2640
ctctttgaac atcaacggtg tagaggatta taaatcaatc tttgacggtg acggaaaaac    2700
gtatcaaaat gtacagcagt tcatcgatga aggcaactac agctcaggcg acaaccatac    2760
gctgagagat cctcactacg tagaagataa aaggccacaaa tacttagtat ttgaagcaaa    2820
cactggaact gaagatggct accaaggcga agaatcttta tttaacaaag catactatgg    2880
caaaagcaca tcattcttcc gtcaagaaag tcaaaaactt ctgcaaagcg ataaaaaacg    2940
cacggctgag ttagcaaacg gcgctctcgg tatgattgag ctaaacgatg attacacact    3000 gaaaaagtg atgaaaccgc tgattgcatc taacacagta acagatgaaa ttgaacgcgc    3060
gaacgtcttt aaaatgaacg gcaaatggta ccctgttcact gactcccgcg atcaaaaat    3120 gacgattgac ggcattacgt ctaacgatat ttacatgctt ggttatgttt ctaattcttt    3180
aactggccca tacaagccgc tgaacaaaac tggccttgtg ttaaaaatgg atcttgatcc    3240
taacgatgta acctttactt actcacactt cgctgtacct caagcgaaag gaaacaatgt    3300
cgtgattaca agctatatga caaacagagg attctacgca gacaaacaat caacgtttgc    3360
gccaagcttc ctgctgaaca tcaaaggcaa gaaaacatct gttgtcaaag acagcatcct    3420
tgaacaagga caattaacag ttaacaaata aaaacgcaaa agaaaatgcc gatnnccggt    3480
ttattgacta ccggaagcag tgtgaccgtg tgcttctcaa atgcctcagg ctgtctatgt    3540
gtgactgttg agctgtaaca agttgtctca ggtgttcaat tcatgttct agttgctttg    3600 ttttactggt ttcacctgtt ctattaggtg ttacatgctg ttcatctgtt acattgtcga    3660
tctgttcatg gtgaacagct ttaaatgcac caaaaactcg taaaagctct gatgtatcta    3720 tctttttac accgttttca tctgtgcata tggacagttt tcccttttgat gctagcttgc    3780 atgcctgcag gtcgactcta gaggatcccc gtactatcaa caggttgaac tgcggatctt    3840
```

```
gcggccagct ttatgcttgt aaaccgtttt gtgaaaaaat ttttaaaata aaaaggggga    3900
cctctagggt ccccaattaa ttagtaatat aatctattaa aggtcattca aaaggtcatc    3960
caccggatca attcccctgc tcgcgcaggc tgggtgccaa gctctcgggt aacatcaagg    4020
cccgatcctt ggagcccttg ccctcccgca cgatgatcgt gccgtgatcg aaatccagat    4080
ccttgacccg cagttgcaaa ccctcactga tccggctcac ggtaactgat gccgtatttg    4140
cagtaccagc gtacgcccca cagaatgatg tcacgctgaa aatgccggcc tttgaatggg    4200
ttcatgtgca gctccatcag caaaagggga tgataagttt atcaccaccg actatttgca    4260
acagtgccgt tgatcgtgct atgatcgact gatgtcatca gcggtggagt gcaatgtcgt    4320
gcaatacgaa tggcgaaaag ccgagctcat cggtcagctt ctcaaccttg gggttacccc    4380
cggcggtgtg ctgctggtcc acagctcctt ccgtagcgtc cggcccctcg aagatgggcc    4440
acttggactg atcgaggccc tgcgtgctgc gctgggtccg ggagggacgc tcgtcatgcc    4500
ctcgtggtca ggtctggacg acgagccgtt cgatcctgcc acgtcgcccg ttacaccgga    4560
ccttggagtt gtctctgaca cattctggcg cctgccaaat gtaaagcgca gcgcccatcc    4620
atttgccttt gcggcagcgg ggccacaggc agagcagatc atctctgatc cattgcccct    4680
gccacctcac tcgcctgcaa gcccggtcgc ccgtgtccat gaactcgatg gcaggtact    4740 tctcctcggc gtgggacacg atgccaacac gacgctgcat cttgccgagt tgatggcaaa    4800
ggttccctat ggggtgccga cacactgcac cattcttcag gatggcaagt tggtacgcgt    4860
cgattatctc gagaatgacc actgctgtga gcgctttgcc ttggcggaca ggtggctcaa    4920
ggagaagagc cttcagaagg aaggtccagt cggtcatgcc tttgctcggt tgatccgctc    4980
ccgcgacatt gtggcgacag ccctgggtca actgggccga gatccgttga tcttcctgca    5040
tccgccagag ggcgggatgc gaagaatgcg atgccgctcg ccagtcgatt ggctgagctc    5100
atgagcggag aacgagatga cgttggaggg gcaaggtcgc gctgattgct ggggcaacac    5160
gtgaaaggcg agatcaccaa ggtagtcggc aaataatgtc taacaattcg ttcaagccga    5220
cgccgcttcg cggcgcggct taactcaagc gttagatgca ctaagcacat aattgctcac    5280
agccaaacta tcaggtcaag tctgctttta ttatttttaa gcgtgcataa taagccctac    5340
acaaattggg agatatatca tgaaaggctg cttttttctt gttatcgcaa tagttggcga    5400
agtaatcgca acatccgcat taaaatctag cgagggcttt actaagctga tccggtggat    5460
gaccttttga atgaccttta atagattata ttactaatta attggggacc ctagaggtcc    5520 cctttttat tttaaaaatt ttttcacaaa acggtttaca agcataaagc tcgatgaatt    5580
gatccgaagt tccattctc tagaaagtat aggaacttcg aattgtcgac aagctccccg    5640
gggagcttga tctggcttat cgaaattaat acgactcact atagggagac cggaattcgt    5700
aatcatggtc atagctgttt cctgtgtgaa attgttatcc gctcacaatt ccacacaaca    5760
tacgagccgg aagcataaag tgtaaagcct ggggtgccta atgagtgagc taactcacat    5820
taattgcgtt gcgctcactg cccgctttcc agtcgggaaa cctgtcgtgc cagctgcatt    5880
aatgaatcgg ccaacgcgcg gggagaggcg gtttgcgtat tgggcgctct tccgcttcct    5940
cgctcactga ctcgctgcgc tcggtcgttc ggctgcggcg agcggtatca gctcactcaa    6000
aggcggtaat acggttatcc acagaatcag gggataacgc aggaaagaac atgtgagcaa    6060
aaggccagca aaaggccagg aaccgtaaaa aggccgcgtt gctggcgttt ttccataggc    6120
tccgcccccc tgacgagcat cacaaaaatc gacgctcaag tcagaggtgg cgaaacccga    6180
caggactata aagataccag gcgtttcccc ctggaagctc cctcgtgcgc tctcctgttc    6240
```

```
cgaccctgcc gcttaccgga tacctgtccg cctttctccc ttcgggaagc gtggcgcttt    6300
ctcaaagctc acgctgtagg tatctcagtt cggtgtaggt cgttcgctcc aagctgggct    6360
gtgtgcacga accccccgtt cagcccgacc gctgcgcctt atccggtaac tatcgtcttg    6420
agtccaaccc ggtaagacac gacttatcgc cactggcagc agccactggt aacaggatta    6480
gcagagcgag gtatgtaggc ggtgctacag agttcttgaa gtggtggcct aactacggct    6540
acactagaag aacagtattt ggtatctgcg ctctgctgaa gccagttacc ttcggaaaaa    6600
gagttggtag ctcttgatcc ggcaaacaaa ccaccgctgg tagcggtggt ttttttgttt    6660
gcaagcagca gattacgcgc agaaaaaaag gatctcaaga agatcctttg atctttcta    6720 cggggtctga cgctcagtgg aacgaaaact cacgttaagg gattttggtc atgagattat    6780
caaaaaggat cttcacctag atccttttaa attaaaaatg aagttttaaa tcaatctaaa    6840
gtatatatga gtaaacttgg tctgacagtt accaatgctt aatcagtgag gcacctatct    6900
cagcgatctg tctatttcgt tcatccatag ttgcctgact ccccgtcgtg tagataacta    6960
cgatacggga gggcttacca tctggcccca gtgctgcaat gataccgcga gacccacgct    7020
caccggctcc agatttatca gcaataaacc agccagccgg aagggccgag cgcagaagtg    7080
gtcctgcaac tttatccgcc tccatccagt ctattaattg ttgccgggaa gctagagtaa    7140
gtagttcgcc agttaatagt ttgcgcaacg ttgttgccat tgctacaggc atcgtggtgt    7200
cacgctcgtc gtttggtatg gcttcattca gctccggttc ccaacgatca aggcgagtta    7260
catgatcccc catgttgtgc aaaaaagcgg ttagctcctt cggtcctccg atcgttgtca    7320
gaagtaagtt ggccgcagtg ttatcactca tggttatggc agcactgcat aattctctta    7380
ctgtcatgcc atccgtaaga tgcttttctg tgactggtga gtactcaacc aagtcattct    7440
gagaatagtg tatgcggcga ccgagttgct cttgcccggc gtcaatacgg gataataccg    7500
cgccacatag cagaacttta aaagtgctca tcattggaaa acgttcttcg gggcgaaaac    7560
tctcaaggat cttaccgctg ttgagatcca gttcgatgta acccactcgt gcacccaact    7620
gatcttcagc atcttttact ttcaccagcg tttctgggtg agcaaaaaca ggaaggcaaa    7680
atgccgcaaa aaagggaata agggcgacac ggaaatgttg aatactcata ctcttccttt    7740
ttcaatatta ttgaagcatt tatcagggtt attgtctcat gagcggatac atatttgaat    7800
gtatttagaa aaataaacaa ataggggttc cgcgcacatt tccccgaaaa gtgccacctg    7860
acgtctaaga aaccattatt atgatgacat taacctataa aaataggcgt atcacgaggc    7920
cctttcgtc                                                            7929
```

<210> SEQ ID NO 34
<211> LENGTH: 4163
<212> TYPE: DNA
<213> ORGANISM: Escherichia coli
<220> FEATURE:
<221> NAME/KEY: gene/kan,sacB
<222> LOCATION: (1)..(4163)
<223> OTHER INFORMATION: Plasmid pWG162; template in PCR for kan, sacB
    genes

<400> SEQUENCE: 34

```
tcgagaggcc tgacgggatt taaatcgcta gcgggctgct aaaggaagcg gaacacgtag     60
aaagccagtc cgcagaaacg gtgctgaccc cggatgaatg tcagctactg ggctatctgg    120
acaagggaaa acgcaagcgc aaagagaaag caggtagctt gcagtgggct tacatggcga    180
tagctagact gggcggtttt atggacagca agcgaaccgg aattgccagc tggggcgccc    240
```

```
tctggtaagg ttgggaagcc ctgcaaagta aactggatgg ctttcttgcc gccaaggatc      300
tgatggcgca ggggatcaag atctgatcaa gagacaggat gaggatcgtt tcgcatgatt      360
gaacaagatg gattgcacgc aggttctccg gccgcttggg tggagaggct attcggctat      420
gactgggcac aacagacaat cggctgctct gatgccgccg tgttccggct gtcagcgcag      480 ggcgcccgg ttcttttgt caagaccgac ctgtccggtg ccctgaatga actgcaggac      540
gaggcagcgc ggctatcgtg gctggccacg acgggcgttc cttgcgcagc tgtgctcgac      600
gttgtcactg aagcgggaag ggactggctg ctattgggcg aagtgccggg gcaggatctc      660
ctgtcatctc accttgctcc tgccgagaaa gtatccatca tggctgatgc aatgcggcgg      720
ctgcatacgc ttgatccggc tacctgccca ttcgaccacc aagcgaaaca tcgcatcgag      780
cgagcacgta ctcggatgga agccggtctt gtcgatcagg atgatctgga cgaagagcat      840
caggggctcg cgccagccga actgttcgcc aggctcaagg cgcgcatgcc cgacggcgag      900
gatctcgtcg tgacccatgg cgatgcctgc ttgccgaata tcatggtgga aaatggccgc      960
ttttctggat tcatcgactg tggccggctg ggtgtggcgg accgctatca ggacatagcg     1020
ttggctaccc gtgatattgc tgaagagctt ggcggcgaat gggctgaccg cttcctcgtg     1080
ctttacggta tcgccgctcc cgattcgcag cgcatcgcct tctatcgcct tcttgacgag     1140
ttcttctgag cgggactctg gggttcgaaa tgaccgacca agcgacgccc aacctgccat     1200
cacgagattt cgattccacc gccgccttct atgaaaggtt gggcttcgga atcgttttcc     1260
gggacgccgg ctgatgatc ctccagcgcg gggatctcat gctggagttc ttcgcccacg     1320
ctagtttaaa caccccgagt ccactgagcg tcagacccct aataagatg atcttcttga     1380 gatcgttttg gtctgcgcgt aatctcttgc tctgaaaacg aaaaaaccgc cttgcagggc     1440 ggttttttcga aggttctctg agctaccaac tctttgaacc gaggtaactg gcttggagga     1500
gcgcagtcac caaaacttgt cctttcagtt tagccttaac cggcgcatga cttcaagact     1560
aactcctcta aatcaattac cagtggctgc tgccagtggt gcttttgcat gtctttccgg     1620
gttggactca agacgatagt taccggataa ggcgcagcgg tcggactgaa cggggggttc     1680
gtgcatacag tccagcttgg agcgaactgc ctacccggaa ctgagtgtca ggcgtggaat     1740
gagacaaacg cggccataac agcggaatga caccggtaaa ccgaaaggca ggaacaggag     1800
agcgcacgag ggagccgcca gggggaaacg cctggtatct ttatagtcct gtcgggtttc     1860
gccaccactg atttgagcgt cagatttcgt gatgcttgtc agggggggcgg agcctatgga     1920 aaaacggctt tgccgcggcc ctctcacttc cctgttaagt atcttcctgg catcttccag     1980
gaaatctccg ccccgttcgt aagccatttc cgctcgccgc agtcgaacga ccgagcgtag     2040
cgagtcagtg agcgaggaag cggaatatat cctgtatcac atattctgct gacgcaccgg     2100
tgcagccttt tttctcctgc cacatgaagc acttcactga caccctcatc agtgccaaca     2160
tagtaagcca gtatacactc cgctagcgca tgcatccatt taaatggaag aaataaaaga     2220
aaatgccaat aggatattgg cattttcttt tgcgttttta tttgttaact gttaattgtc     2280
cttgttcaag gatgctgtct ttgacaacag atgttttctt gcctttgatg ttcagcagga     2340
agctcggcgc aaacgttgat tgtttgtctg cgtagaatcc tctgtttgtc atatagcttg     2400
taatcacgac attgtttcct ttcgcttgag gtacagcgaa gtgtgagtaa gtaaaggtta     2460
catcgttagg atcaagatcc attttttaaca caaggccagt tttgttcagc ggcttgtatg     2520
ggccagttaa agaattagaa acataaccaa gcatgtaaat atcgttagac gtaatgccgt     2580
```

-continued

| | |
|---|---|
| caatcgtcat ttttgatccg cgggagtcag tgaacaggta ccatttgccg ttcatttaa | 2640 |
| agacgttcgc gcgttcaatt tcatctgtta ctgtgttaga tgcaatcagc ggtttcatca | 2700 |
| cttttttcag tgtgtaatca tcgtttagct caatcatacc gagagcgccg tttgctaact | 2760 |
| cagccgtgcg tttttatcg ctttgcagaa gttttgact ttcttgacgg aagaatgatg | 2820 |
| tgcttttgcc atagtatgct tgttaaata aagattcttc gccttggtag ccatcttcag | 2880 |
| ttccagtgtt tgcttcaaat actaagtatt tgtggccttt atcttctacg tagtgaggat | 2940 |
| ctctcagcgt atggttgtcg cctgagctgt agttgccttc atcgatgaac tgctgtacat | 3000 |
| tttgatacgt ttttccgtca ccgtcaaaga ttgatttata atcctctaca ccgttgatgt | 3060 |
| tcaaagagct gtctgatgct gatacgttaa cttgtgcagt tgtcagtgtt tgtttgccgt | 3120 |
| aatgtttacc ggagaaatca gtgtagaata acggatttt tccgtcagat gtaaatgtgg | 3180 |
| ctgaacctga ccattcttgt gtttggtctt ttaggataga atcatttgca tcgaatttgt | 3240 |
| cgctgtcttt aaagacgcgg ccagcgtttt tccagctgtc aatagaagtt tcgccgactt | 3300 |
| tttgatagaa catgtaaatc gatgtgtcat ccgcatttt aggatctccg gctaatgcaa | 3360 |
| agacgatgtg gtagccgtga tagtttgcga cagtgccgtc agcgttttgt aatggccagc | 3420 |
| tgtcccaaac gtccaggcct tttgcagaag agatatttt aattgtggac gaatcaaatt | 3480 |
| cagaaacttg atattttca ttttttgct gttcagggat ttgcagcata tcatggcgtg | 3540 |
| taatatggga aatgccgtat gttcctatt atggctttg gttcgtttct ttcgcaaacg | 3600 |
| cttgagttgc gcctcctgcc agcagtgcgg tagtaaaggt taatactgtt gcttgttttg | 3660 |
| caaactttt gatgttcatc gttcatgtct cctttttat gtactgtgtt agcggtctgc | 3720 |
| ttcttccagc cctcctgttt gaagatggca agttagttac gcacaataaa aaaagaccta | 3780 |
| aaatatgtaa ggggtgacgc caaagtatac actttgccct ttacacattt taggtcttgc | 3840 |
| ctgctttatc agtaacaaac ccgcgcgatt tacttttcga cctcattcta ttagactctc | 3900 |
| gtttggattg caactggtct attttcctct ttgtttgat agaaaatcat aaaggattt | 3960 |
| gcagactacg ggcctaaaga actaaaaaat ctatctgttt cttttcattc tctgtatttt | 4020 |
| ttatagtttc tgttgcatgg gcataaagtt gcctttaa tcacaattca gaaaatatca | 4080 |
| taatatctca tttcactaaa taatagtgaa cggcaggtat atgtgatggg ttaaaaagga | 4140 |
| tcggcggccg ctcgatttaa atc | 4163 |

<210> SEQ ID NO 35
<211> LENGTH: 3350
<212> TYPE: DNA
<213> ORGANISM: Escherichia coli
<220> FEATURE:
<221> NAME/KEY: gene/pykF
<222> LOCATION: (1)..(3350)
<223> OTHER INFORMATION: Plasmid pGW191; used in the deletion of pykF

<400> SEQUENCE: 35

| | |
|---|---|
| gggcgaattg ggcccgacgt cgcatgctcc cggccgccat ggcggccgcg ggaattcgat | 60 |
| acattcctct gcacgctttt tcgatgtcac ctatccttag agcgaggcac caccactttc | 120 |
| gtaataccgg attcgctttc cggcagtgcg cccagaaagc aagtttctcc catccttctc | 180 |
| aacttaaaga ctaagactgt catgaaaaag accaaaattg tttgcaccgc atctgttcac | 240 |
| gtcctgtaat attgcttttg tgaattaatt tgtatatcga agcgccctga tgggcgcttt | 300 |
| ttttatttaa tcgataacca gaagcaataa aaaatcaaat cggatttcac tatataatct | 360 |
| cactttatct aagatgaatc cgatggaagc atcctatcac tagtgaattc gcggccgcct | 420 |

```
gcaggtcgac catatgggag agctcccaac gcgttggatg catagcttga gtattctata    480
gtgtcaccta aatagcttgg cgtaatcatg gtcatagctg tttcctgtgt gaaattgtta    540
tccgctcaca attccacaca acatacgagc cggaagcata agtgtaaag cctggggtgc    600
ctaatgagtg agctaactca cattaattgc gttgcgctca ctgcccgctt tccagtcggg    660
aaacctgtcg tgccagctgc attaatgaat cggccaacgc gcgggagag gcggtttgcg    720
tattgggcgc tcttccgctt cctcgctcac tgactcgctg cgctcggtcg ttcggctgcg    780
gcgagcggta tcagctcact caaaggcggt aatacggtta ccacagaat caggggataa    840
cgcaggaaag aacatgtgag caaaaggcca gcaaaaggcc aggaaccgta aaaaggccgc    900
gttgctggcg ttttttccata ggctccgccc cctgacgag catcacaaaa atcgacgctc    960
aagtcagagg tggcgaaacc cgacaggact ataaagatac caggcgtttc ccctggaag   1020
ctccctcgtg cgctctcctg ttccgaccct gccgcttacc ggatacctgt ccgcctttct   1080
cccttcggga agcgtggcgc tttctcatag ctcacgctgt aggtatctca gttcggtgta   1140
ggtcgttcgc tccaagctgg gctgtgtgca cgaaccccc gttcagcccg accgctgcgc   1200
cttatccggt aactatcgtc ttgagtccaa cccggtaaga cacgacttat cgccactggc   1260
agcagccact ggtaacagga ttagcagagc gaggtatgta ggcggtgcta cagagttctt   1320
gaagtggtgg cctaactacg gctacactag aagaacagta tttggtatct gcgctctgct   1380
gaagccagtt accttcggaa aaagagttgg tagctcttga tccggcaaac aaaccaccgc   1440
tggtagcggt ggtttttttg tttgcaagca gcagattacg cgcagaaaaa aaggatctca   1500
agaagatcct ttgatctttt ctacggggtc tgacgctcag tggaacgaaa actcacgtta   1560
agggattttg gtcatgagat tatcaaaaag gatcttcacc tagatccttt taaattaaaa   1620
atgaagtttt aaatcaatct aaagtatata tgagtaaact tggtctgaca gttaccaatg   1680
cttaatcagt gaggcaccta tctcagcgat ctgtctattt cgttcatcca tagttgcctg   1740
actccccgtc gtgtagataa ctacgatacg ggagggctta ccatctggcc ccagtgctgc   1800
aatgataccg cgagacccac gctcaccggc tccagattta tcagcaataa accagccagc   1860
cggaagggcc gagcgcagaa gtggtcctgc aactttatcc gcctccatcc agtctattaa   1920
ttgttgccgg gaagctagag taagtagttc gccagttaat agtttgcgca acgttgttgc   1980
cattgctaca ggcatcgtgg tgtcacgctc gtcgtttggt atggcttcat tcagctccgg   2040
ttcccaacga tcaaggcgag ttacatgatc ccccatgttg tgcaaaaaag cggttagctc   2100
cttcggtcct ccgatcgttg tcagaagtaa gttggccgca gtgttatcac tcatggttat   2160
ggcagcactg cataattctc ttactgtcat gccatccgta agatgctttt ctgtgactgg   2220
tgagtactca accaagtcat tctgagaata gtgtatgcgg cgaccgagtt gctcttgccc   2280
ggcgtcaata cgggataata ccgcgccaca tagcagaact ttaaaagtgc tcatcattgg   2340
aaaacgttct cggggcgaaa actctcaag gatcttaccg ctgttgagat ccagttcgat   2400
gtaacccact cgtgcaccca actgatcttc agcatctttt actttcacca gcgtttctgg   2460
gtgagcaaaa acaggaaggc aaaatgccgc aaaaaaggga ataagggcga cacggaaatg   2520
ttgaatactc atactcttcc ttttttcaata ttattgaagc atttatcagg gttattgtct   2580
catgagcgga tacatatttg aatgtattta gaaaaataaa caataggggg ttccgcgcac   2640
atttccccga aaagtgccac ctgatgcggt gtgaaatacc gcacagatgc gtaaggagaa   2700
aataccgcat caggaaattg taagcgttaa tattttgtta aaattcgcgt taaatttttg   2760
```

```
ttaaatcagc tcattttta accaataggc cgaaatcggc aaaatccctt ataaatcaaa      2820
agaatagacc gagatagggt tgagtgttgt tccagtttgg aacaagagtc cactattaaa      2880
gaacgtggac tccaacgtca aagggcgaaa aaccgtctat cagggcgatg gcccactacg      2940
tgaaccatca ccctaatcaa gttttttggg gtcgaggtgc cgtaaagcac taaatcggaa      3000
ccctaaaggg agcccccgat ttagagcttg acggggaaag ccggcgaacg tggcgagaaa      3060
ggaagggaag aaagcgaaag gagcgggcgc tagggcgctg gcaagtgtag cggtcacgct      3120
gcgcgtaacc accacacccg ccgcgcttaa tgcgccgcta cagggcgcgt ccattcgcca      3180
ttcaggctgc gcaactgttg ggaagggcga tcggtgcggg cctcttcgct attacgccag      3240
ctggcgaaag ggggatgtgc tgcaaggcga ttaagttggg taacgccagg gttttcccag      3300
tcacgacgtt gtaaaacgac ggccagtgaa ttgtaatacg actcactata              3350
```

```
<210> SEQ ID NO 36
<211> LENGTH: 78
<212> TYPE: DNA
<213> ORGANISM: Artificial Sequence
<220> FEATURE:
<223> OTHER INFORMATION: Synthetic PCR Primer 87A

<400> SEQUENCE: 36 atgaaaaga ccaaaattgt ttgcaccatc ggaccgaaaa ccgaatctga agagatgtct      60
agcgcatgca tccattta                                                   78

<210> SEQ ID NO 37
<211> LENGTH: 79
<212> TYPE: DNA
<213> ORGANISM: Artificial Sequence
<220> FEATURE:
<223> OTHER INFORMATION: Synthetic PCR Primer 87B

<400> SEQUENCE: 37
ttacaggacg tgaacagatg cggtgttagt agtgccgctc ggtaccagtg caccagaaag      60
gcgaagaact ccagcatga                                                  79

<210> SEQ ID NO 38
<211> LENGTH: 20
<212> TYPE: DNA
<213> ORGANISM: Artificial Sequence
<220> FEATURE:
<223> OTHER INFORMATION: Synthetic PCR Primer 78A

<400> SEQUENCE: 38
acacattcct ctgcacgctt                                                 20

<210> SEQ ID NO 39
<211> LENGTH: 20
<212> TYPE: DNA
<213> ORGANISM: Artificial Sequence
<220> FEATURE:
<223> OTHER INFORMATION: Synthetic PCR Primer 78B

<400> SEQUENCE: 39
aggatgcttc catcggattc                                                 20
```

ENGINEERING MICROBES FOR EFFICIENT PRODUCTION OF CHEMICALS

CROSS-REFERENCE TO RELATED APPLICATIONS

The application is the U.S. national stage application of International Patent Application No. PCT/US2010/057119, which claims the priority of the U.S. Provisional Application Ser. No. 61/281,481, filed on Nov. 18, 2009.

The Sequence Listing for this application is labeled "SeqList.txt" which was created on Nov. 16, 2010 and is 240 KB. The entire content of the sequence listing is incorporated herein by reference in its entirety.

GOVERNMENT SUPPORT

This invention was made with United States Government support under a contract awarded from the US Department of Energy under Award Number DE-EE0002878/001. The United States Government has certain rights in the invention.

BACKGROUND OF THE INVENTION

During the last ten years, with an explosion in our knowledge about microbial genomes, biochemical pathways within the cell, metabolic flux analysis, microarray analysis and in silico analysis, industrial microbiology has ventured into manufacturing chemicals from renewable feedstock using biocatalysts.

A 2004 U.S. Department of Energy report, entitled "Top value added chemicals from biomass", has identified 15 building block chemicals that can be produced from renewable feedstocks using biocatalysts. The 15 building blocks are 1,4-diacids (succinic, fumaric and malic), 2,5-furan dicarboxylic acid, 3-hydroxypropionic acid, aspartic acid, glucaric acid, glutamic acid, itaconic acid, levulinic acid, 3-hydroxybutyrolactone, glycerol, sorbitol, xylitol, and arabinitol. Of these 15 chemicals identified by U.S. Department of Energy, succinic acid production at industrial scale using biocatalysts has advanced significantly (Kurzrock and Weuster-Botz, 2009; Lee et al., 2008; Andersson, et al., 2007; Lu et al., 2009; US Patent Application Publication No. 2006/0073577).

The bacteria residing in the rumen of the cattle are known to produce succinic acid under anaerobic growth conditions. A number of rumen bacteria such as *Actinobacillus succinogens*, *Anaerobiospirillum succiniproducens* and *Mannheimia succiniproducens* have been isolated and developed as biocatalysts for succinic acid production. *Escherichia coli* strains capable of producing succinic acid in titers, rates, and yields that approach commercial feasibility have also been constructed using the combined knowledge of microbial carbon metabolism and microbial genetics. U.S. Pat. No. 7,223, 567 describes construction of *E. coli* strain SBS550MG producing succinic acid in a rich growth medium. U.S. Pat. No. 6,455,284 describes the construction of an *E. coli* strain with an exogenous pyruvate carboxylase gene as a biocatalyst for succinic acid production. Pyruvate carboxylase is absent in wild type *E. coli* strains. The pyruvate carboxylase gene obtained from other microbial organisms such as *Rhizobium elti* can be expressed under a constitutive promoter to enhance succinic acid production. PCT Patent Application Nos. WO/2008/115958 and WO/2010/115067 describe the construction of *E. coli* strain KJ122, which is a biocatalyst for succinic acid production in minimal growth medium.

To achieve commercially attractive biosynthetic production of succinic acid and other chemicals, further genetic manipulations are necessary. There is still a need to improve the overall "efficiency" (defined as including, but not limited to, titer, rate, and yield) of production of succinate and other chemicals by microorganisms by means of manipulating the biochemical pathways inside the cell using novel genetic approaches. To the extent that chemical production is coupled to cell growth, an increase in efficiency of succinic acid or other chemical production can also be achieved by means of improving the rate of growth of the microbial cells that produce the desired chemical. The maximum theoretical yield for succinic acid production in *E. coli* is calculated to be 1.714 mol of succinic acid per 1 mol of glucose providing a mass yield of 1.12 gram of succinic acid for one gram of glucose consumed (Vemuri, et al., 2002).

U.S. Patent Application Publication No. 2008/0009041 describes an *E. coli* strain comprising chromosomal DNA that is at least 470 kb shorter than that of wild-type *E. coli* strain. This mutant *E. coli* strain accumulates more cell mass and exhibits significant increase in the amount of threonine accumulated.

U.S. Patent Application Publication 2009/0075333 also describes an *E. coli* strain with reduced genome size having one or more of equal or improved growth rate, transformation efficiency, protein expression, DNA production, DNA yield and/or DNA quality compared to the parental strain.

U.S. Patent Application Publication 2009/0221055 describes a novel *Bacillus subtilis* mutant strain having good productivity of various enzymes derived via gene disruption.

These approaches of reducing the genome size to achieve increased growth rate is based on the fact that the bacterium growing in the fermentor includes many non-essential genes which can be deleted. The bacterium living in a natural environment has many condition-responsive genes to provide mechanisms for surviving difficult environmental conditions of temperature, stress, or lack of food source. Replicating these genes, which are unnecessary in the fermentor, requires expenditure of cellular energy that could be conserved otherwise in the absence of these unnecessary genes.

While the approach of reducing the genome size may be useful for improving the growth performance of the strains producing recombinant proteins, nucleic acid and amino acid, it has not been shown to be a useful approach to improve the performance of strains to produce other chemicals such as succinic acid, fumaric acid, and malic acid, which are intermediates in the Krebs cycle (also known as the tricarboxylic acid cycle or TCA cycle). The efficiency of production of these and other chemicals also depends on the rate of flow of carbon through different paths in the central metabolic pathways and, in some cases, upon achieving a favorable redox balance during anaerobic or microaerobic growth.

The U.S. Patent Application Publication 2009/0075352, and Lee et al (2005) describe a method for improving a bacterial strain based on in-silico analysis. In this approach, the genomic sequence of *Mannheimia succiniproducens*, which produces succinic acid in significant quantities, is compared with the genomic sequence of *E. coli* to identify optimal genes to be deleted in *E. coli* for the purpose of converting a wild type *E. coli* strain into a succinic acid producing strain. Although this approach looks attractive on the surface, it remains to be seen whether the genetic information derived from *M. succiniproducens* can be extrapolated to *E. coli* to achieve a commercially viable succinate production strain. The recommended deletions from the above cited US patent application were a combination of ptsG, pykA, and pykF. However, the succinate titer actually achieved from such a strain was only 8.16 mM (0.96 g/l), which is nowhere near the level needed for commercially attractive production, and growth of the strain was very poor. Moreover, a combination of deletion mutations (pykA, pykF, and ptsHI) similar to that recommended in the application referenced above has been reported earlier, and the resulting strain grew very poorly on glucose (Ponce, et al., 1995). Thus, the combination of mutations described by Lee et al (2005) were not sufficient to construct a commercially viable strain, and the mutations were not tested in a strain context that could prove that they were necessary or appropriate for a commercially viable strain. Therefore, for one skilled in the art, there is not a clear path from the above disclosures to a commercially viable succinate production strain, which will need to grow well on glucose or other inexpensive carbon source and produce at least 20 g/l succinate (170 mM).

In order to compete with petrochemical processes for chemical syntheses, there is a need in the art for developing more efficient biocatalysts for chemical production. The first step is to identify genetic changes in the host chromosome that could contribute to an enhanced chemical production. In view of this circumstance, an object of the present invention is to identify novel mutations that can be used to improve chemical production by microbial strains selected for industrial use. In a specific embodiment, an objective of the present invention is to improve the efficiency of microbial production of organic acids. In a more specific embodiment, the objective is to improve the efficiency of succinic acid production. In another aspect of the invention, the objective is to learn how, in general, to rationally improve production of chemicals such as succinic acid from microbes without having to resort to labor-intensive methods such as metabolic evolution.

A type of reverse engineering has been performed on *Corynebacterium glutamicum* strains that have been mutagenized and screened for high lysine production. The genome of a highly altered lysine production strain is compared to that of the wild type strain, and the differences were used to re-engineer a minimally mutated strain (Ikeda et al., 2006). However, several hundreds of mutations were found, and although only a few of these seemed to play a major role in lysine overproduction, it would be highly impractical to test all of the several hundred mutations for relevance. On the surface, the invention disclosed herein might seem to be similar to what is disclosed in this prior art, a major difference is that the starting strain of the present invention was not mutagenized, but rather allowed to mutate spontaneously, and it was not screened, but rather selected in a process of metabolic evolution. This results in at least two major differences that distinguish the present invention: (1) the density of mutations is far lower, by almost two orders of magnitude, and (2) all eight of the mutations tested in the present invention proved to be relevant for either improved growth or improved efficiency of chemical production. Thus the methods and materials of the present invention are much improved over those of the prior art.

BRIEF SUMMARY OF THE INVENTION

The present invention provides microorganisms having improved ability to produce chemicals such as succinic acid.

The present invention also provides a method of constructing microorganisms having improved ability to produce chemicals such as succinic acid.

The present invention also provides a method for producing succinic acid using the microorganisms having improved ability to produce chemicals such as succinic acid.

In one embodiment of the present invention, a microorganism having improved ability to produce chemicals such as succinic acid and having a mutated pykA gene is provided.

In another embodiment of the present invention, a microorganism having improved ability to produce chemicals such as succinic acid and having a mutated pykF gene is provided.

In yet another embodiment of the present invention, a microorganism having improved ability to produce chemicals such as succinic acid and having mutated pykA and pykF genes is provided.

In one embodiment of the present invention, a microorganism having improved ability to produce chemicals such as succinic acid and having an inactivated or mutated galS gene is provided.

In one embodiment of the present invention, a microorganism having improved ability to produce chemicals such as succinic acid and having an inactivated or mutated galR gene is provided.

In another embodiment of the present invention, a microorganism having improved ability to produce succinic acid and having multiple copies of galP gene is provided.

In yet another embodiment of the present invention, a microorganism having improved ability to produce succinic acid, multiple copies of galP gene and a mutated phosphotransferase system (PTS) for glucose transport into the cell is provided.

In yet another embodiment of the present invention, a microorganism having improved ability to produce chemicals such as succinic acid and a deletion of a large region of the genome comprising multiples genes including genes ydcC through ydcF in a 48 kb region of chromosomal DNA is provided.

In one embodiment of the present invention, a microorganism having improved ability to produce chemicals such as succinic acid and a missense mutation in the rpoA gene is provided.

In yet another embodiment of the present invention, a microorganism having improved ability to produce chemicals such as succinic acid and a mutation at amino acid position 322 of the rpoA gene is provided.

In yet another embodiment of the present invention, a microorganism having improved ability to produce chemicals such as succinic acid and a proline to leucine mutation at amino acid position 322 of the rpoA gene is provided.

In yet another embodiment of the present invention, a microorganism having improved ability to produce chemicals such as succinic acid and a mutation in the rpoC gene is provided.

In yet another embodiment of the present invention, a microorganism having improved ability to produce chemicals such as succinic acid and a mutation in the F region of rpoC gene is provided.

In yet another embodiment of the present invention, a microorganism having improved ability to produce chemicals such as succinic acid and a missense mutation in the amino acid at position 747 in the F region of rpoC gene is provided.

In yet another embodiment of the present invention, a microorganism having an improved ability to produce chemicals such as succinic acid and a methionine to isoleucine mutation at position 747 in the F region of rpoC gene is provided.

In one embodiment of the present invention, a microorganism having an improved ability to produce chemicals such as succinic acid and having a mutation in the gldA gene is provided.

In one embodiment of the present invention, a microorganism having an improved ability to produce chemicals such as succinic acid and having a mutation in the ftsI gene is provided.

In yet another embodiment of the present invention, a microorganism having an improved ability to produce chemicals such as succinic acid and having mutation in the dhaM gene is provided.

BRIEF DESCRIPTION OF THE DRAWINGS

No drawings are included in this application.

DETAILED DESCRIPTION OF THE INVENTION

Disclosed in this present invention are the microorganisms suitable for the production of succinic acid through a fermentative process. Although the present invention provides a process for the production of succinic acid in commercially significant quantities from carbon compounds by genetically modified bacterial strains, the teachings of the present invention are equally applicable to the industrial production of a number of other chemicals.

For the purpose of the description of the present invention, the following definitions shall be used.

A number of industrially useful chemicals can be manufactured using the present invention. Examples of such chemicals include, but are not limited to, ethanol, butanols, lactate, succinate, fumarate, malate, threonine, methionine and lysine. Since organic acids can exist both as free acids and as salts (for example, but not limited to, salts of sodium, potassium, magnesium, calcium, ammonium, chloride, sulfate, carbonate, bicarbonte, etc), chemical names such as succinic acid, fumaric acid, malic acid, aspartic acid, threonine, methionine, and lysine shall be meant to include both the free acid and any salt thereof. Likewise, any salt, such as succinate, fumarate, malate, aspartate, etc., shall be meant to include the free acid as well.

The present invention combines the technique of specific genetic modifications with the process of metabolic evolution to obtain strains showing high yield, titer and volumetric productivity for succinic acid production under anaerobic or microaerobic growth conditions in mineral salt medium with a carbohydrate substrate.

As used in the present invention, the term "titer" means the molar concentration of a particular compound in the fermentation broth. Thus in the fermentation process for the production of succinic acid according to the present invention, a succinic acid titer of 100 mM would mean that the fermentation broth at the time of measurement contained 100 mMoles of succinic acid per liter of fermentation broth.

As used in the present invention, the term "yield" refers to the moles of a particular compound produced per mole of the feedstock consumed during the fermentation process. Thus in the fermentative process for the production of succinic acid using glucose as the feedstock, the term yield refers to the number of moles of succinic acid produced per mole of glucose consumed.

As used in the present invention, the term "volumetric productivity" refers to the amount of a particular compound in grams produced per unit volume per unit time. Thus a volumetric productivity value of 0.9 g $L^{-1}h^{-1}$ for succinic acid would mean that 0.9 gram succinic acid is accumulated in one liter of fermentation broth during an hour of growth.

The terms "genetically engineered" or "genetically modified" as used herein refers to the practice of altering the expression of one or more enzymes in the microorganisms through manipulating the genomic DNA of the microorganisms.

As used in the present invention, the term "gene" includes the open reading frame of the gene as well as the upstream and downstream regulatory sequences. The upstream regulatory region is also referred to as the promoter region of the gene. The downstream regulatory region is also referred to as the terminator region.

"Allele" is one of two or more forms of DNA sequence of a particular gene. Each gene without any mutation is referred as a wild type allele when compared to a corresponding gene that has a mutation.

A "Homolog" is a gene related to a second gene by descent from a common ancestral DNA sequence. The term, homolog, may apply to the relationship between genes separated by the event of speciation or to the relationship between genes separated by the event of genetic duplication. "Orthologs" are genes in different species that evolved from a common ancestral gene by speciation. Normally, orthologs retain the same function in the course of evolution. Identification of orthologs is critical for reliable prediction of gene function in newly sequenced genomes. Speciation is the origin of a new species capable of making a living in a new way from the species from which it arose. As part of this process it has also acquired some barrier to genetic exchange with the parent species. "Paralogs" are genes related by duplication within a genome. Orthologs retain the same function in the course of evolution, whereas paralogs evolve new functions, even if these are related to the original one.

The phrase "functionally similar" means broadly any wild type or mutated DNA sequence, gene, enzyme, protein, from any organism, that has a biological function that is equivalent or similar to any wild type or mutated DNA sequence, gene, enzyme, protein that is found in the same or a different organism by the methods disclosed herein. Functionally similarity need not require sequence homology. For example, in this invention, we find that a mutation in pykA that reduces, but does not eliminate, total pyruvate kinase activity in *E. coli*, leads to more efficient succinate production. By extension, a mutation in another type of organism, for example the yeast *Saccharomyces*, that reduces pyruvate kinase, is functionally similar, and the relevant gene in *Saccharomyces*, for example, the PYK1 or PYK2 gene, would be functionally similar to the pykA gene of *E. coli*.

A gene or protein with "altered activity" is broadly defined as gene or protein that produces a measurable difference in a measurable property when compared to the relevant wild type gene or protein. The altered activity could manifest itself in a general way by increasing or decreasing the growth rate or efficiency of succinate production of the strain containing the altered gene or protein. Other measurable properties include, but are not limited to enzyme activity, substrate specificity of an enzyme, kinetic parameters of an enzyme such as affinity for a substrate or rate, stability of an enzyme, regulatory properties of an enzyme, gene expression level, regulation of gene expression under various conditions, etc.

As used in the present invention, the term mutation refers to genetic modifications done to the gene including the open reading frame, upstream regulatory region and downstream regulatory region. The gene mutations result either in an up regulation or a down regulation or complete inhibition of the transcription of the open reading frame of the gene. The gene mutations are achieved either by deleting the entire coding region of the gene or a portion of the coding nucleotide sequence or by introducing a frame shift mutation, a missense mutation, or insertion, or by introducing a stop codon or combinations thereof. Mutations may occur in the structural genes coding for the proteins directly involved in the biological functions such as enzyme reactions or transport of the organic molecules across the cell membrane. Alternately, mutations may occur in the regulatory genes coding for the proteins which control the expression of the genes coding for the proteins directly involved in the biological functions. The proteins which control the expression of the other genes are referred to as regulatory proteins and the genes coding for these regulatory proteins are referred to as regulatory genes.

"Mutation" shall also include any change in a DNA sequence relative to that of the relevant wild type organism. For example, a mutation found in strain KJ122 is any change in a DNA sequence that can be found when the DNA sequence of the mutated region is compared to that of the parent wild type strain, *E. coli* C, also known as ATCC 8739. A mutation can be an insertion of additional DNA of any number of base pairs or a deletion of DNA of any number of base pairs. A particular type of insertion mutation is a gene duplication. A gene can be duplicated by a spontaneous mutational event, in which the second copy of the gene can be located adjacent to the original copy, or a gene can be duplicated by genetic engineering, in which the second copy of the gene can be located at a site in the genome that is distant from the original copy. A mutation can be a change from one base type to another base type, for example a change from an adenine to a guanine base. In the vernacular of genetics, a mutation can be a missense (which changes the amino acid coded for by a codon), a nonsense (which changes a codon into stop codon), a frameshift (which is an insertion or deletion of a number of bases that is not a multiple of three and which changes the reading frame and alters the amino acid sequence that is encoded downstream from the mutation, and often introduces a stop codon downstream from the mutation), or an inversion (which results from a DNA sequence being switched in polarity but not deleted).

A "null mutation" is a mutation that confers a phenotype that is substantially identical to that of a deletion of an entire open reading frame of the relevant gene, or that removes all measurable activity of the relevant gene.

A "mutant" is a microorganism whose genome contains one or more mutations.

As used in this invention, the term "exogenous" is intended to mean that a molecule or an activity derived from outside of a cell is introduced into the host microbial organism. In the case an exogenous nucleic acid molecule introduced into the microbial cell, the introduced nucleic acid may exist as an independent plasmid or may get integrated into the host chromosomal DNA. The exogenous nucleic acid coding for a protein may be introduced into the microbial cell in an expressible form with its own regulatory sequences such as promoter and terminator sequences. Alternatively, the exogenous nucleic acid molecule may get integrated into the host chromosomal DNA and may be under the control of the host regulatory sequences.

The term "endogenous" refers to the molecules and activity that are present within the host cell. When used in reference to a biosynthetic activity, the term "exogenous" refers to an activity that is introduced into the host reference organism. The source can be, for example, a homologous or heterologous encoding nucleic acid that expresses the referenced activity following introduction into the host microbial organism. If the nucleic acid coding for a protein is obtained from the same species of the microbial organism, it is referred as homologous DNA. If the nucleic acid is derived from a different microbial species, it is referred as heterologous DNA. Irrespective of the nature of the DNA, whether it is homologous or heterologous, when introduced into a host cell, the DNA as well as the activity derived form that introduced DNA is referred as exogenous. Therefore, exogenous expression of an encoding nucleic acid of the invention can utilize either or both heterologous and homologous encoding nucleic acid.

"Microorganism" shall include any bacterium, archeon, yeast, filamentous fungus, unicellular alga, or dinoflagellate.

The recombinant microorganisms suitable for this present invention are derived from a number of bacterial families, preferably from the Enterobacteriaceae family. The suitable microorganisms are selected form the genera *Escherichia, Erwinia, Providencia,* and *Serratia*. The genus *Escherichia* is particularly preferred. Within the genus *Escherichia*, the species *Escherichia coli* is particularly preferred. Any one strain of *E. coli* such as *E. coli* B, *E. coli* C, *E. coli* W, or the like is useful for the present invention.

*E. coli* strains capable of producing organic acids in significant quantities are well known in the art. For example, the U.S. Patent Application Publication No. 2009/0148914 provides strains of *E. coli* as a biocatalyst for the production of chemically pure acetate and/or pyruvate. The U.S. Pat. No. 7,629,162 provide derivatives of *E. coli* K011 strain constructed for the production of lactic acid. International Patent Applications published under the Patent Cooperation Treaty Nos. WO 2008/115958 and WO 2010/115067 provide microorganism engineered to produce succinate and malate in minimal mineral salt medium containing glucose as a source of carbon in pH-controlled batch fermentation.

In some other embodiments of the invention, bacteria that can be modified according to the present invention include, but are not limited to, *Achromobacter delmarvae, Achromobacter viscosus, Achromobacter lacticum, Actinomadura madurae, Actinomyces violaceochromogenes, Aeromonas salmonicida, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Bacillus amyloliqyefaciens, Bacillus coagulans, Bacillus circulans, Bacillus licheniformis, Bacillus pumilus, Bacillus subtilis, Bacillus thiaminol yticus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Citrobactor freundii, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Escherichia freundii, Flavobacterium peregrinum, Flavobacterium fucatum, Flavobacterium aurantinum, Flavobacterium rhenanum, Flavobacterium sewanense, Flavobacterium breve, Flavobacterium meningosepticum, Gluconobacter oxydans, Gluconobacter asaii, Kitasatosporia parulosa, Klebsiella oxytoca, Klebsiella pneumonieae, Microbacterium ammoniaphilum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Serratia marcescens, Sporosarcina ureae, Staphylococcus aureus, Streptomyces coeli-* color, *Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Salmonella typhimurium, Salmonella schottmulleri, Vibrio metschnikovii, Vibrio tyrogenes, Xanthomonas citri* and so forth.

The present invention provides genetically modified bacterial strains showing impressive titers, high yield and significant volumetric productivity for succinic acid when grown under fermentative conditions in minimal salt medium containing a carbon source as the substrate for fermentation process. The microorganisms of the subject invention can be employed in a single step production process using various sugars such as hexoses, pentoses, disaccharides and other carbon compounds such as glycerol.

The term "fermentation" and "ferment" in some contexts suggests anaerobic growth or metabolism by an organism. However, in this disclosure, we shall use the terms "fermentation" and "ferment" to refer broadly to commercial or experimental growth of a microorganisms under any condition, including aerobic, anaerobic, or microaerobic, or a combination thereof.

Biosynthetic production of many chemicals can proceed more efficiently (for example, at higher yield) when the growth of the production organism is carried out under conditions where oxygen or air is absent or limited. This is largely because the presence of oxygen generally results in the metabolism of carbon sources into carbon dioxide, a relatively low value byproduct. Fermentation in the absence of a deliberate feeding of oxygen or air is usually called "anaerobic". However, achieving strict anaerobic conditions is costly and sometimes difficult to attain. Moreover, for some fermentations, strict anaerobic conditions are not necessary or sometimes not optimal. For fermentations where oxygen or air is not made strictly absent, or where oxygen or air is deliberately fed at a low, controlled rate, we shall use the term "microaerobic".

The microorganisms suitable for the practice of the present invention can be grown aerobically (in the presence of oxygen) or anaerobically (in the complete absence of oxygen) or microaerobically (with a minimal amount of oxygen supply). In the preferred embodiment of the present invention, the microorganism selected for the production of succinic acid is grown in an anaerobic condition. Alternatively, the microorganisms suitable for the present invention can be grown in a dual-phase growth regime, wherein the microorganism is initially grown in an aerobic growth condition to reach a certain level of cell growth before transferring it to the anaerobic growth condition to achieve the production of succinic acid in commercially significant quantities. During the dual-phase growth for the production of succinic acid by the microorganisms of the present invention, production and the accumulation of the succinic acid occurs during the anaerobic fermentative growth phase.

In the present invention, unique and advantageous combinations of gene mutations have been employed to direct the carbon flow to succinic acid production. In addition, the succinic acid production is coupled with microbial growth which in turn is coupled to cellular ATP level and redox balance.

The term "redox balance" refers to the ability of the cell to maintain the appropriate ratio of NADH to $NAD^+$. In other words, the cells are able to oxidize the NADH so that there is enough $NAD^+$ to oxidize the carbohydrate substrates during the anaerobic fermentative growth. During aerobic growth, the $NAD^+$ pool is regenerated through oxidative phosphorylation involving NADH. However, under anaerobic growth conditions the regeneration of the $NAD^+$ pool is achieved only by means of manipulating the flow of carbon through various metabolic pathways inside the cell which can oxidize NADH.

"Carbon catabolite repression" refers broadly to any biological system in which the expression of one or more genes is regulated in part by the source of carbon on which the organism grows. For example, in *E. coli*, genes that function in gluconeogenesis in a wild type organism are repressed by the presence of glucose in the medium. In particular, the pck gene is down regulated by glucose in most wild type *E. coli* strains. As another example, in wild type strains of the yeast *Saccharomyces cerevisiae*, utilization of carbon sources other than glucose, such as galactose, is inhibited by the presence of glucose in the medium.

The "tricarboxylic acid cycle" or "TCA" cycle is a set of biochemical reactions that exists in most microorganisms, in whole or in part. In many organisms, for example eubacteria and yeasts, the TCA cycle runs as a true cycle during aerobic growth. In this case, the TCA cycle has two main functions, to catabolize two carbon units (such as acetate) into carbon dioxide, and to generate biochemical intermediates for biosynthesis, such as glutamate, succinate, and aspartate. During anaerobic or microaerobic growth, the TCA cycle might not run as a true cycle, but rather as one or more linear pathways. For example, under conditions of low oxygen in *E. coli*, the TCA cycle enzymes operate as a two-branched pathway, comprising a so-called reductive pathway that leads to succinate through malate, and a so-called oxidative pathway that leads to a-ketoglutarate through citrate. In this case, the function of the TCA cycle is primarily to produce the biochemical intermediates glutamate, succinate, and aspartate. Some carbon can be transferred between the two branches by the glyoxylate shunt. During aerobic, anaerobic, and micoraerobic growth, for each molecule of a biochemical intermediate that is used for biosynthesis, a molecule in the TCA cycle must be replaced, otherwise the compounds in the cycle will become depleted. This replacement reaction is called an anapleurotic reaction.

The common anapleurotic reactions take a three carbon compound, such as pyruvate or phosphoenol pyruvate (PEP), and convert it into a four carbon compound such as oxaloacetate or malate, using carbon dioxide as a second substrate.

In many organisms, such as eubacteria and yeasts, the expression of genes that encode enzymes of the TCA cycle and glyoxylate shunt are repressed by glucose and/or induced by oxygen (Cronan and Laporte, 1996). The control of this regulation is complex. According to the literature, efficient production of succinate and other compounds, especially under conditions of low oxygen, requires a delicate balancing of the reductive TCA cycle enzymes and those of the glyoxylate shunt (Vemuri et al., 2002; Wang et al., 2006; Sanchez et a12005).

However, the state of the art has not been advanced enough to rationally design strains to make optimal, or close to optimal, use of the TCA cycle and glyoxylate shunt paths for biosynthesis of compounds such as succinate. One of the objectives of the present invention is to dissect at the level of DNA sequence a highly evolved microorganism that is close to optimal for production of a chemical of the TCA cycle, so that in the future, a more rational strain design and construction can be used to engineer strains for production of succinate and other chemicals. The mutations discovered in the present invention are useful for improving the biosynthesis of chemicals related to the TCA cycle, including TCA cycle intermediates, and derivatives of TCA cycle intermediates, particularly chemicals derived from oxaloacetate, including, but not limited to succinate, fumarate, malate, glutamate, aspartate, threonine, lysine, methionine, and isoleucine, because the mutations described herein are useful for increasing metabolic flux toward and from oxaloacetate under conditions of low oxygen in a glucose (or other sugar) based medium, where in a wild type organism, the genes and enzymes that function to produce such compounds are negatively regulated in complex ways.

One mechanism for the transport of sugars that is frequently found in bacteria is the phosphotransferase system (PTS). This is composed of two-energy-coupling proteins, Enzyme I and HPr, and several sugar-specific Enzyme II proteins or protein complexes, which typically consist of three protein domains, EIIA, EIIB and EIIC. The organization of the EII domains differs between bacteria. EII may consist of a single fused protein or different fused and unfused domains. The translocation of the specific sugar through the membrane is facilitated by the integral membrane domain(s) EIIC and sometimes EIID. However, it is the complex of the three enzyme domains or proteins, functioning together, which brings about the transport and phosphorylation of the sugar substrate, resulting in an intracellular pool of phosphorylated carbohydrate. The source of energy and phosphate for the PTS is phosphoenol pyruvate (PEP). However, PEP can also be a substrate for biosynthesis of many four-carbon compounds, such as malate, fumarate, succinate, aspartate, and other compounds made from those four-carbon compounds, so there can be competition inside the cell for PEP between the PTS and biosynthetic pathways. In $E.$ $coli$, the PTS system for glucose is coded for by the ptsH,I,G, and crr genes. There are other mechanisms for transporting sugars into microorganisms that do not involve the PTS. We shall call the proteins involved in these other transport mechanisms that do not directly use PEP as a substrate, "non-PTS" sugar transporters. Examples of non-PTS transporters are proton symporters, such as GalP and XylE of $E.$ $coli$, facilitated diffusers such as HEX1,2,6, and 7 of $Saccharomyces$ $cerevisiae$ and Glf of $Zymomonas$ $mobilis$, and ABC-type transporters, such as XylFGH of $E.$ $coli$.

The largest group of sugar transporters in the bacteria is known as ATP binding cassette (ABC) transporters. As the name implies, the ABC transporters require a molecule of ATP for every molecule of sugar transported into the bacterial cell. XylFGH is an ABC transporter for the transport of xylose, a pentose sugar, into the cell. AraFGH is an ABC transporter for the transport of arabinose, yet another pentose sugar.

The other type of non-PTS bacterial sugar transporters are grouped under Major Facilitator Super family (MFS). Within the MFS sugar transporters, two different categories of transporter are recognized. MFS includes Ht linked symporters, $Na^+$-linked symporters-antiporters and uniporters. The uniporters are simple facilitators for the sugar transport. The trans-membrane protein Glf in $E.$ $coli$ is an example of uniporter. The $H^+$-symporters require a proton for every sugar molecule transported into the cell. The GalP protein in $E.$ $coli$ is a symporter for the transport of galactose, a hexose sugar, into the cell. GalP is a very well characterized symporter with 12 trans-membrane loops. GalP is also reported to have the ability to transport glucose across the cell membrane. AraE is a proton-linked symporter for the transport of arabinose across the cell membrane. Similarly XylE protein is a proton-linked symporter for the transport of xylose.

The elimination of glucose uptake by the phosphotransferase system (PTS) could help in reducing the energy spent on glucose uptake into the microbial cell. The energy conserved by manipulating the PTS can be channeled to improve the efficiency of organic acid production. The phosphotransferase system genes ptsH and ptsG can be manipulated to conserve the energy in glucose uptake and thereby improve the efficiency of succinic acid production by the microorganism. Thus by mining the data available in the area of microbial metabolic pathways, one can delete a set of genes so as to block most of the metabolic pathways and channel the carbon flow to the production of succinic acid with great efficiency. With the inhibition of PTS-mediated glucose uptake, other systems for glucose uptake can be activated to assure the continued availability of glucose within the cell for the production of the industrially useful chemicals. For example, the glf gene coding for glucose permease, a glucose uniporter, has been shown to substitute for the loss of PTS mediated glucose uptake. Similarly the over expression of galP and glk genes are reported to enhance the glucose uptake and phosphorylation in a pts⁻ strain of $E.$ $coli$. GalP is a symporter for the uptake of galactose, a hexose sugar. GalP has been reported to transport glucose in a pts⁻ strain. The significance of GalP mediated glucose uptake is evidenced by the fact that the inactivation of galP gene in a pts⁻ mutant is found to be lethal (Yi et al., 2003). Glk is necessary to achieve the phosphorylation of the glucose molecule before it can enter into glycolysis. The expression of the GalP protein in a pts⁻ strain can be achieved either by expressing an exogenous gene under a constitutive promoter or by means of relieving the repression of the galP expression through mutations in genes coding for a repressor of the galP gene such as galS and galR.

Using our current understanding about the metabolic pathways in a microbial cell, it is possible to rationally construct a strain that is designed to produce succinic acid in significant amounts. The rational design for the construction of an efficient succinic acid producing microorganism is based on the assumption that succinic acid could accumulate under anaerobic or micro-aerobic conditions when the other potential fermentative pathways for carbon flow inside the cell are blocked through genetic manipulation. The genetic manipulations required to block a particular pathway for carbon flow within the cell involve reducing or removing the activity one or more genes coding for the enzymes involved in the operation of the pathway that is desired to be blocked. The carbon flow to acetate, formate, ethanol and lactate can be blocked through appropriate genetic methods. For example, by deleting the gene for adhE, the anaerobic alcohol production can be blocked, and the carbon flow to acetate can be blocked by deleting the ack and/or ptaA genes.

Although it is straight forward in principle to block specific unwanted pathways for carbon flow within the cell and to channel the carbon flow to succinic acid production, in practice the rationally designed gene deletions do not result in the desired phenotype. As described by Jantama et at (2008a; 2008b), the rationally designed gene deletions resulted initially in bacterial strains with poor growth. The gene-deleted strains with poor growth were subsequently subjected to metabolic evolution to improve the growth rate. Thus, in constructing an $E.$ $coli$ strain for succinic acid production, a first round of deletions that removed ldhA, adhE, and ack genes were made, followed by a first stage of metabolic evolution.

After the first stage of metabolic evolution, a second round of gene deletions removed the focA and pflB genes. Then a second round of metabolic evolution was performed. In a third round of deletion, the mgsA gene was removed. Then a third stage of metabolic evolution was performed. In the fourth round of deletion, the poxB gene is deleted was removed. Then a fourth stage of metabolic evolution was performed.

"Metabolic evolution" is a process whereby a culture (usually, but not necessarily, a liquid culture) of an organism (often a genetically engineered organism) is subjected to repeated cycles of dilution and re-growth (called "transfers"), so that after a number of transfers, it is possible to obtain a strain possessing improved growth properties and/or improved production of a chemical that is coupled to growth, such as succinic acid, lactic acid, ethanol, or a butanol. Metabolic evolution is particularly effective as a method for strain improvement when growth of a microorganism is made to be dependent on producing a desired chemical by fermentation. For example, a heterofermentative microorganism such as wild type E. coli, when grown anaerobically or microaerobically on a sugar such as glucose, produces a mixture of chemicals, D-lactate, L-lactate, formate, succinate, acetate, carbon dioxide, hydrogen, and ethanol. The pathways to these compounds are called "fermentative pathways". In other organisms, fermentative pathways can lead to a great variety of chemicals, such as butanols, other alcohols, other organic acids, esters, 3-hydroxy alkanoic acids, fatty acids, alkanes, alkenes, carotenoids, amino acids, vitamins, and many more. Of the compounds made by wild type E. coli, at least D-lactate, succinate, and ethanol are of commercial interest, and so can be considered to be a "desired compound". By deleting genes that control the pathways to the unwanted compounds, the organism if left with only one or more pathways to the desired compound, and so growth becomes dependent on, or coupled to, said desired compound. Alternatively, all fermentative pathways from a host organism can be deleted, and a new exogenous pathway from a different organism, that leads to a desired compound that is not naturally produced in the host organisms, can be introduced by genetic engineering. Metabolic evolution can then be applied to the mutated or engineered strain to improve growth and therefore production of a desired compound. Since metabolic evolution does not require deliberate mutagenesis, the mutational load on the evolved strain is minimal, and most, if not all, mutations that accumulate will be beneficial for growth and/or production of the desired compound. A good example of metabolic evolution is strain KJ122, which had been engineered to produce succinate as the desired compound and then subjected to metabolic evolution (Jantama et al., 2008b).

In this specification, the terms "chemical" and "compound" shall be used interchangeably, and both shall be used in the conventional sense.

During metabolic evolution, the selected culture is repeatedly transferred and diluted into fresh minimal medium many times in series to achieve many generations of growth with the attendant competition between clones in which spontaneous mutations occur and become fixed in the population, Some mutations confer more efficient use of the carbon source(s) being fed, better ability to tolerate toxic chemicals in the culture, and higher efficiency of production of a desirable chemical, which in this example was succinic acid. During the metabolic evolution, attention is paid to select clones with the desirable phenotypes, but which also includes low or absent production of undesired byproducts.

Thus, to generalize, a microbial organism designed and genetically engineered to overproduce a particular chemical may not have an appropriate growth rate and consequently may not show the expected or desired efficiency for producing that particular chemical. Metabolic evolution can be used to select for a strain that has improved growth and product tolerance accompanied by an increased rate for the production of that particular chemical. However, since metabolic evolution results from spontaneous mutations, the precise genetic changes that result in improved growth, product tolerance, and efficiency of chemical production might not be obvious, predictable, or reproducible by the metabolic evolution method. Determination of the genomic DNA sequence of the evolved organism can provide the details of the mutations that accumulated. Then, by replacing each individual mutation in the evolved strain with the homologous wild type allele, or alternatively, introducing the mutated allele into a naïve, unevolved strain, followed by comparative analysis of strain performance, one can demonstrate which mutations contribute to the desired phenotype. It is possible that some mutations that remain in the evolved strain are detrimental to the desired process. These could be mutations that were beneficial at an earlier stage in the evolution, or which have not had time to evolve away. In any case, knowing which mutations are beneficial, and the exact nature of those mutations, allows (1) a more rational design for future genetic engineering, for example engineering a new strain or organism for succinic acid production without the need for a lengthy evolution process, and (2) an insight into subtle or unpredicted mutations that improve strain performance, which in turn can lead to further, more rational strain improvements. For example, if a frameshift mutation found in a repressor gene is discovered in an evolved strain, then genetic engineering can be used to create a complete deletion of that repressor gene to create a non-revertable, and therefore more stable, allele that confers the same phenotype.

During the process of metabolic evolution using certain selective pressure to force the organism to acquire a certain desirable phenotype, two possible changes could occur. The organism could simply adapt itself to the selective pressure and not show a changed genotype. Alternatively, the organism might undergo certain genetic changes under selective pressure and exhibit a changed phenotype that is more permanent. When there is only an adaptation and there is no genetic change, the organism will revert back to its original phenotype once the selection pressure is relieved. These organisms are referred to as "adapted" organisms. The "adapted" microorganisms have to undergo another fresh round of selection pressure to show a changed phenotype. On the other hand, when there is an accompanying genetic change, the changed phenotype will continue to exist even when there is no selection pressure. Metabolic evolution accompanied by certain genetic changes is desirable. The microorganism acquiring a stable genetic change during metabolic evolution can be easily identified by means of growing the microorganism in the original growth medium without any selection pressure for some time before transferring it to the fresh medium with the selection pressure. If these organisms are able to show good growth and the expected phenotype without any lag period, the organism is considered to have acquired a changed genotype accompanying the phenotype during metabolic evolution.

In order to make the microorganism to produce succinic acid in significant quantities, various enzymes involved in a number of microbial metabolic pathways including glycolytic pathway, tricarboxylic acid cycle (also known as Krebs cycle or TCA cycle) and glyoxylate shunt can be manipulated using a variety of genetic engineering techniques described in the scientific and patent literature cited and incorporated by references in the paragraphs above. The details about various microbial metabolic pathways can be found in the standard biochemistry text books such as Principles of Biochemistry, by Lehninger and Biochemistry by Lubert Stryer. The Biochemical pathways poster by G. Michael available from Sigma Chemical Company in St. Louis, Mo., USA also provides details about various biochemical pathways with in a bacterial cell.

During aerobic growth, the microbial carbon metabolism involves glycolysis, tricarboxylic acid cycle and oxidative phosphorylation. The reduced enzyme co-factors such as NADPH and NADH are regenerated by the operation of oxidative phosphorylation accompanied by ATP production required for cell growth. Under anaerobic growth conditions for the production of succinic acid in the preferred embodiment of the present invention, the regeneration of reduced cofactors NADPH and NADH is accomplished by directing the carbon flow into the tricarboxylic acid cycle toward succinic acid production and eliminating all of the other fermentative pathways for regeneration of $NADP^+$ and $NAD^+$.

Depending on the type of organic acid preferred, the metabolic pathways are specifically engineered so that the microorganism produces a particular organic acid of our choice. The microorganisms are capable of synthesizing a number of organic acids including lactic acid, acetic acid, malic acid, pyruvic acid, formic acid and succinic acid. Thus in developing a biocatalyst for the production of succinic acid, the pathways for production of acetic acid, lactic acid, pyruvic acid, and formic acid are blocked and the carbon flow to succinic acid production is facilitated through manipulating one or more enzymes involved in the carbon metabolism within the cell. The list of the enzymes that are active in the microbial fermentative pathway which can be manipulated using the known genetic engineering techniques includes, but not limited to, isocitrate synthetase (aceA), malate synthase (aceB), the glyoxylate shunt operon (aceBAK), acetate kinase-phosphotransacetylase (ackA-pta); aconitase hydratase 1 and 2 (acnA and acnB); acetyl-CoA synthetase (acs); citrate lyase (citDEF); alcohol dehydrogenase (adhE); citrate synthase (citZ); fumarate reductase (frd); lactate dehydrogenases (ldh); malate dehydrogenase (mdh); aceBAK operon repressor (iclR); phosphoenol pyruvate carboxylase (pepC); pyruvate formate lyase (pfl); pyruvate oxidase (poxB); pyruvate carboxy kinase (pck); and pyruvate carboxylase (pyc).

Glycolysis of carbon sources results in the production of phosphoenol pyruvate (PEP). PEP is further metabolized by the mixed acid pathway. As used in the present invention, the term "mixed acid pathway" refers to the flow of carbon from PEP through both the tricarboxylic acid cycle and the various fermentative pathways that are operational under anaerobic conditions. Under anaerobic conditions, at least four different fermentative pathways for the metabolism of pyruvate are recognizable. The pyruvate may be reduced to lactate using the NADH and thereby producing $NAD^+$ to maintain the redox balance of the cell necessary for the continuous metabolism of carbon source. The acetyl-CoA derived from pyruvate may also be reduced to produce ethanol accompanied by the oxidation of NADH to produce $NAD^+$. Pyruvate may also be converted into formate or acetate.

Within the TCA cycle, two different arms are recognized. In one arm of the TCA cycle referred as the oxidative arm encompassing the carbon flow from oxaloacetate to succinic acid through isocitrate, the $NADP^+$ is utilized to oxidize isocitrate with the resulting formation of NADPH. In the other arm of the TCA cycle referred as the reductive arm of the TCA cycle encompassing the flow of carbon from oxaloacetate to succinic acid through malate and fumarate, the NADH is oxidized to produce $NAD^+$ and thereby helping the cell to maintain the redox balance.

In one embodiment of the present invention, the carbon flow from PEP through fermentative pathways is prevented by mean of inactivating the genes coding for the enzymes involved in the fermentative pathways. The genes suitable for blocking the carbon flow through these fermentative pathways include ldhA, pflB, adhE, pta, ackA, and poxB. The elimination of one or more of these genes is expected to reduce the carbon flow from PEP through the fermentative pathways. In another aspect of the present invention, the mgsA gene coding for the methylglyoxal synthase (mgsA) responsible for the conversion of methylglyoxal to lactic acid is inactivated beside the inactivation of six other genes involved in the fermentative pathways.

In yet another embodiment of the present invention, the functional homologues of the genes involved in the fermentative pathway are also inactivated besides inactivating the genes well known to be involved in one or other fermentative pathway. A propionate kinase with acetate kinase activity is encoded by the tdcD gene which is produced only for the degradation of threonine. However, during the anaerobic growth with 10% (w/v) glucose, the expression of tdcD could functionally replace ackA. In addition, the adjacent tdcE gene in the same operon is similar to pflB and encodes α-ketobutyrate formate lyase with pyruvate formate-lyase activity. In one aspect of the present invention, the tdcDE genes are inactivated to prevent the entry of carbon into fermentative pathways and to assure the flow of carbon into the TCA cycle.

In another embodiment of the present invention, besides blocking the carbon flow through fermentative pathways, the carbon flow within the TCA cycle is altered so that there is carbon flow directed towards the production of succinic acid. In one aspect of the present invention the manipulation of carbon flow within the TCA cycle is achieved by means of up-regulating the expression of one or more genes. In yet another aspect of the present invention, one or more genes functioning within TCA cycle may be inactivated to facilitate an increased carbon flow to succinic acid.

In a preferred aspect of the present invention, the gene mdh encoding for malate dehydrogenase is up regulated to improve the conversion of malate to fumarate and succinate. The flow of the carbon from oxaloacetate to succinic acid through malate and fumarate is referred as the reductive arm of the TCA cycle. The flow of carbon through this reductive arm of the TCA cycle from oxaloacetic acid to succinic acid would consume two moles of NADH for every mole of succinic acid produced and thereby help in maintaining the redox balance of the cell under anaerobic condition. In other words, the up-regulation of mdh would help in regenerating the $NAD^+$ required to maintain the redox balance of the cell. The up-regulation of mdh gene expression can be achieved by means of replacing the native promoter for mdh gene with some other strong promoter sequence or alternatively by means of mutating the promoter region of the mdh gene so that there is an increase transcription of mdh gene. Alternatively, additional copies of the mdh gene can be added to the strain, or genes regulating the expression of the mdh gene can be manipulated to increase expression of the mdh gene. In a preferred embodiment of the present invention, the up regulation of mdh gene expression is achieved by means of genetically manipulating its promoter region.

In the regular operation of TCA cycle, succinic acid is produced through the operation of oxidative of arm of the TCA cycle. The flow of carbon from oxaloacetate to succinic acid through citrate, cis-aconitate, isocitrate, α-ketoglutarate, and succinyl-CoA is referred as the oxidative arm of the TCA cycle. The succinic acid can also be produced through the operation of the glyoxylate bypass. During the operation of glyoxylate bypass, by the action of isocitrate lyase, succinate and glyoxylate are produced from isocitrate. The succinate thus produced from the operation of oxidative arm of the TCA cycle or from the operation of the glyoxylate bypass, can be acted upon by succinate dehydrogenase (sdh) to yield fumaric acid and then malic acid. Therefore, in yet another embodiment of the present invention, gene inactivation can be used to prevent the dehydrogenation of the succinate in order to increase the intracellular succinic acid production.

In yet another aspect of the present invention, the carbon flow through the glyoxylate bypass can be manipulated to achieve an increase in the succinic acid production. Isocitrate lyase enzyme catalyzes the cleavage of isocitrate to glyoxylate and succinate. Isocitrate lyase is coded by the aceBAK operon. The isocitrate lyase activity is suppressed by iclR genes. In other words, the expression of iclR gene prevents the operation of glyoxylate shunt. In one aspect of the present invention, the iclR gene is inactivated beside the inactivation of the genes involved in the fermentative metabolism.

In yet another embodiment of the present invention, besides preventing the operation of the fermentative pathways and increasing the flow of carbon within the TCA cycle towards succinic acid production through genetic manipulations, the outward carbon flow from the TCA cycle to other metabolic pathways can also be blocked through genetic means to increase the succinic acid production. For example, the flow of carbon from the TCA cycle into amino acid metabolism can be blocked in order to improve the carbon flow towards succinic acid. The aspartate aminotransferase gene (aspC) transfers the amino group from glutamic acid to oxaloacetic acid in the synthesis of aspartic acid and thereby facilitates the outward flow of carbon from the TCA cycle. In one aspect of the present invention, the inactivation of the aspC gene is followed to block the outward flow of carbon from the TCA cycle in order to improve the carbon flow from oxaloacetate towards succinic acid production either through the oxidative or reductive arm of the TCA cycle.

The other outward flow of the carbon from TCA cycle occurs from malate. The decarboxylation of malate by malic enzyme (sfcA) results in the production of pyruvate. In one aspect of the present invention, the gene coding for the sfcA gene is inactivated to curtail the outward flow of carbon from TCA cycle. In yet another aspect of the present invention, both aspC and sfcA genes are inactivated to prevent the outward flow of carbon from TCA cycle so as to enhance the succinic acid accumulation.

In yet another aspect of the present invention, the outward flow of carbon from TCA cycle is prevented by inactivating the citrate lyase gene (citDEF) responsible for the cleavage of citric acid into oxaloacetate and acetate.

Besides inactivating the genes involved in the fermentative pathways and their functional analogues, the growth coupled succinic acid yield can be further improved by genetic manipulations of carboxylating enzymes within the microbial cells. While characterizing the changes that occurred during the metabolic evolution through conducting genetic and enzyme analysis, it has been shown that the carboxylating enzymes within the cell could be yet another target for genetic manipulation to achieve an improved succinic acid yield.

The glycolytic intermediates phosphoenol pyruvate (PEP) and pyruvic acid can be carboxylated to improve the carbon flow into the TCA cycle. Under normal conditions, the carbon entry into the TCA cycle is accomplished by the action of citrate synthase which combines the acetyl-CoA derived from pyruvate with oxaloacetate, an intermediate in TCA cycle, to produce citric acid. By means of improving the efficiency of one or more carboxylating enzymes present within the cell, it is possible to carboxylate phosphoenol pyruvate and pyruvate to oxaloacetate, a TCA cycle intermediate. The oxaloacetate thus produced from the carboxylating reaction can be further reduced through the reductive arm of the TCA cycle to produce succinic acid.

Manipulating the carboxylating enzymes present within the cell is a method to increase the succinic acid yield during anaerobic fermentative growth. It is well known in the art that by means of introducing pyruvate carboxylase (pyc) from an exogenous source it is possible to carboxylate pyruvate to oxaloacetic acid. The microbial strains well suited for genetic manipulations such as E. coli do not have the pyc gene. The pyc genes derived from other bacterial species such as Rhizopium elti and Lactobacillus lacti have been introduced into the genetically modified E. coli strains to improve succinic acid production.

Four different endogenous carboxylating enzymes are known in E. coli. Two of these enzymes are responsible for carboxylating phosphoenol pyruvate and two other enzymes are responsible for the carboxylation of pyruvate derived from phosphoenol pyruvate derived from the action of pyruvate kinase enzyme. The enzyme phosphoenol pyruvate carboxylase (ppc) carboxylates phosphoenol pyruvate to oxaloacetate which could enter into the reductive arm of the TCA cycle to produce succinate. The second carboxylating enzyme phosphoenol pyruvate kinase (pck) also carboxylates phosphoenol pyruvate to produce oxaloacetate, but normally catalyzes the reverse reaction as it is not expressed in the presence of glucose. The two other carboxylating enzymes namely NADH-linked maleic enzyme (maeB) and the NADPH-linked maleic enzyme (maeA/sfcA) carboxylate pyruvic acid to malic acid. The maeB and sfcA enzymes carboxylate the pyruvate derived from phosphoenol pyruvate by the action of pyruvate kinase.

Any one of the four carboxylating enzymes present in the cell can be genetically manipulated to increase its enzymatic activity in order to improve the carbon flow from glycolytic cycle intermediates into the TCA cycle. Of the four native carboxylating enzymes present in E. coli, the PPC-catalyzed reaction is strongly favored. Energy contained in PEP is lost in this reaction with the release of inorganic phosphate. The other three carboxylating enzymes, namely pck, maeA and sfcA (maeB), are not expected to function during the fermentative growth using glucose as the substrate as these three carboxylating enzymes are repressed by glucose. These three carboxylating enzymes are thought to function in the reverse direction during gluconeogenesis when the cells are oxidatively metabolizing organic acids.

The gluconeogenic PEP carboxykinase (pck) can be genetically manipulated to improve the flow of carbon into the TCA cycle. The advantage in improving the activity of pck lies in the fact that this enzyme while carboxylating phosphoenol pyruvate to oxaloacetate, results in the production of a molecule of ATP for every molecule of oxaloacetate produced. An increase in the ATP yield would increase the growth rate of the cells.

The recruitment of the native gluconeogenic pck for fermentative succinate production can be achieved by any mutation that positively affects the transcription of the pck gene. An increase in the level of PCK activity can be achieved by means of expressing the pck gene in a multicopy plasmid with a native promoter or any other promoter sequence which is known to increase the gene's expression. Another way to increase the expression of the pck gene within the cell is to integrate additional copies of the pck gene. In another embodiment of the present invention, the native promoter of the pck gene can be replaced by some other promoter elements known to enhance the level of activity. An increased expression of pck gene can also be achieved either by mutation in the promoter region of the gene or by genetic manipulation of the regulatory elements that are known to interact with the promoter region of the pck gene. The gene coding for a regulator protein of the pck gene can be mutated or deleted or overexpressed in some way in order to increase the expression of pck gene. A single point mutation (G to A transition at position—64 relative to the ATG start codon of pck gene) could increase the transcription of the pck gene accompanied by a corresponding increase in the phosphoenol pyruvate carboxykinase enzyme activity. A similar increase in the pck gene expression can also be achieved by genetically manipulating the genes coding for the proteins known to regulate the expression of pck gene. For example, Cra protein has been shown to activate the expression of pck gene in *E. coli* (Saier and Ramseier, 196). Similarly the csrA system (comprising csrA, csrB, csrC, csrD, uvrY or barA) has also been reported to regulate the level of pck and other genes involved in glucose metabolism by altering mRNA stability (Babitzke and Romeo, 2007; Pernestig et al., 2003; Suzuki K et al., 2002).

In the present invention, the genetically engineered and metabolically evolved strain showing a desirable phenotype, for example, improved efficiency of succinic acid production, and the wild type strain used in the construction of the genetically engineered and metabolically evolved strain are subjected to genomic DNA sequence analysis.

The whole genome sequencing of the wild type parent strain and the genetic engineered and metabolically evolved strains can be accomplished by the sequencing techniques well known to the person experienced in the field of high throughput DNA sequencing. A number of sequencing technologies are available in the market place which could provide genomic sequence information in a cost-effective manner, for example hardware, software, and methods provided by Illumina, Inc., and 454, Inc.

The sequence data obtained from the wild type and evolved bacterial strains can be compared using appropriate software and the genetic changes between the two strains can be obtained. From the list of all of the genetic changes between the two strains, the genetic changes intentionally introduced at the stage of genetic engineering can be verified, and the additional genetic changes that arose and were fixed during the process of metabolic evolution can be identified.

Once the mutations that occurred during the metabolic evolution are identified, the importance of these mutations in improving the production of a desired chemical is determined by using a reverse genetic analysis. For example, a naïve bacterial strain that produces succinic acid at measurable titers and comprising a minimal number of gene changes in its chromosomal DNA can be utilized. The *E. coli* strain XZ722, and the identical published strain XZ721, both comprising mutated forms of pck and pstI and a deletion in pflB, among other strains, are suitable for this purpose (Zhang et al., 2009). A genetic mutation that occurred during metabolic evolution of strain KJ122 (or any other strain of interest) can be installed in strain XZ721 or XZ722 using techniques well known in the art. Two step gene replacement methods are well known in the art (Zhang et al., 2009a; Zhang et al., 2009b; Jantama et al., 2008a; Jantama et al., 2008b). For the "two step gene replacement method" used to construct strains of the present invention, the first step is to install a selectable and counter-selectable cassette containing a drug resistance gene, such as cat (resistance to chloramphenicol at 30 mg/l) or kan (kanamycin resistance at 50 mg/l), together with the sacB gene from *Bacillus subtilis*, which confers sensitivity to 60 g/l sucrose. The cat-sacB or kan-sacB cassette is obtained by PCR using pLOI4151 (SEQ ID NO. 33) or pGW162 (SEQ ID NO. 34) as template, respectively. The PCR primers contain, in addition to about 18 to 25 bases of priming sequences, about 50 bases of homology to the 5' and 3' ends of the chromosomal target sequence, to foster homologous recombination. The linear PCR product is transformed by electroporation into a recipient strain that had been previously transformed with plasmid pKD46, which expresses the phage lambda Red recombinase to increase frequency of integration of the desired PCR fragment in to the chromosome of the recipient strain. pKD46 is selected for by ampicillin resistance at 100 mg/l at 30 degrees C. It has a temperature sensitive origin of replication and can be cured from the host strain by growth at 42 degrees C. pKD46 is described Datsenko and Wanner (2000), and is available from the Coli Genetic Stock Center, Yale University, New Haven, Conn., USA. For the second step of the two step gene replacement method, a second PCR product is made using a second pair of PCR primers that prime at the 5' and 3' ends of the allele that is desired to be installed, using, for example KJ122 chromosomal DNA as a template. This second pair of primers can also contain about 50 base pairs homologous to the 5' and 3' ends of the chromosomal target sequence to foster homologous recombination, similar to the first pair of PCR primers. However, the homologous sequences for the second step can also be simply part of the amplified DNA sequence, if the chromosomal target for the inserted allele is the native locus of the allele to be inserted. In other words, the 50 base pair sequences that are homologous to the chromosomal target are only necessary to be added to the 5' ends of the PCR primers if the chromosomal target is a site different from the native locus of the allele, as in installing a second copy of a gene at a second site in the chromosome. The installation of the changed allele at the second step is accomplished by electroporating the linear second PCR product into the recipient strain (which is the strain that was created in the first step), which still contains pKD46 to stimulate homologous recombination, and selecting on plates containing 60 g/l sucrose. In this two step method, for all manipulations in which homologous recombination is desired, the cells are grown in rich medium containing 5 g/l arabinose to cause expression of the lambda Red recombinase genes from the helper plasmid pKD46. Since spontaneous sacB mutants can arise during the sucrose selection, the resulting colonies are screened for chloramphenicol or kanamycin sensitivity and by diagnostic PCR to identify colonies that have picked up the desired allele change. For subtle mutations, such as point mutations, it is necessary to obtain the DNA sequence of the installed allele to be sure that the desired allele was installed. This can be accomplished by obtaining a PCR amplified copy of the installed allele and sequencing the PCR product. There are many organizations that perform the DNA sequencing as a commercial service, for example the Tufts University Core Facility, Tufts University Medical School, Boston, Mass., USA.

Examples of PCR primers used for two step gene replacements are given in Tables 2.

An alternative approach to determining the effect of each mutation is to replace a single mutant allele in the evolved strain (for example KJ122) with the homologous wild type allele from the parent strain, *E. coli* C (ATCC 8739), using the same two step gene replacement method described above. The strains construction can also be accomplished by generalized bacteriophage transduction, using, for example, phage P1 vir (Silhavy et al., 1984).

Techniques are also well known for creating specific small or large deletions in the *E. coli* chromosome, and these techniques should be applicable to other bacteria, archaea yeasts, and filamentous fungi. For example, Kolisnychenko et al (2002) describe the technology that can be followed to remove specific gene sequence from the chromosomal DNA, and which is hereby incorporated by reference.

After isogenic pairs of strains containing a wild type or mutant allele are constructed, the members of the pair can be tested for growth and chemical production in appropriate small scale fermentors. For example, growth and succinic acid production with pH control under anaerobic or microaerobic conditions can be tested as previously described (Zhang et al., 2009a; Zhang et al., 2008b; Janatama et al., 2008a; Jantama et al., 2008b). For testing strain performance in small scale fermentors, the alkaline solution that is used to neutralize the succinic acid as it is produced can be 2.4 M potassium carbonate plus 1.2 M potassium hydroxide, or alternatively, it can be 6 M ammonium hydroxide plus 3 M ammonium bicarbonate for testing strain performance.

By means of introducing one mutation at a time into a succinate-producing *E. coli* strain such as XZ722, or removing one mutation at a time (i.e. re-introducing the wild type allele of one or more mutated genes) from a succinate-producing strain such as KJ122, one can determine the genetic changes that contribute to improving growth or chemical production. In addition, more than one type of mutation can be introduced or removed into a chemical-producing strain to determine whether there is any additive or synergistic effect due to combinations of mutations. Through this screening of mutations, it is possible to identify mutations that are important to achieve efficient growth and chemical production. Once those novel mutations responsible for improving the chemical production are identified, those mutations can be added to the list of gene modifications that are useful to rationally design a bacterial strain for succinic acid or other chemical production and thereby eliminate the need for the process of metabolic evolution in selecting a strain with desirable phenotype.

In the present disclosure, specific examples are given relating to production of succinate by strains of *E. coli*. However, the principles discovered in the invention have broad applicability, so the mention of specific examples should not be used to limit in any way the broad implications. For example, the finding that a mutation of a particular type in a particular gene is useful for succinate biosynthesis in *E. coli* can be applied without undue experimentation to other bacteria and other organisms. Once a mutation in a gene of interest is identified, a similar mutation, or a mutation that accomplishes the same function or purpose can be introduced into a wide variety of organisms.

For example, the present invention discloses that a decrease in expression of a gene encoding pyruvate kinase is useful for succinate production in the context of a highly developed succinate production strain of *E. coli*. It is now easy to identify a gene that encodes pyruvate kinase in other organisms and decrease expression of that gene in the new organism, by deletion or other mutation, in order to improve succinate production. For close relatives of *E. coli*, such as bacteria of the genus *Klebsiella, Serratia, Citrobacter, Erwinia*, or *Salmonella* a relevant gene can be found easily by a homology search through GenBank or other public database of DNA or protein sequences. Although there is no sharp cutoff that can be used to define what is, or is not, a homolog, a "homolog" of a query sequence is a DNA sequence that is evolutionarily related to a query sequence, and can usually be found 1) as a gene or DNA sequence in which a sequence, or a portion of the sequence, that is 50 or more bases in length has a match of 50% or more identities with the query sequence, allowing for deletions and insertions using the BLASTN program available through GenBank and choosing the default parameters (setting the "Descriptions", "Graphical overview", and "Alignment" settings to 1000 or greater in the Format Request form will produce a larger number of homologs, as will increasing the "Expected" number from the default of 10 to a larger number), or 2) as a protein sequence, or a portion of a protein sequence, that is 25 or more amino acids in length and has 25% or more identity or 50% or more similarity, with the query sequence, allowing for deletions and insertions, using the default parameters of the BLASTP program available through GenBank. When using the GenBank database and the various BLAST programs to perform homology searches, it is sometimes necessary to not select (or to de-select) the genomes of the query's closest relatives. For example, the large number of genomes of members of the genus *Escherichia* can crowd out homologs of *E. coli* queries that exist in more distant relatives such as *Klebsiella* in a homology hit list, but de-selecting the genomes of members of *Escherichia* allows the *Klebsiella* "hits" to be found. For less related organisms, the relevant gene might not be a homolog, or might not be identifiable by DNA or protein sequence homology, but the gene can still be found by a key word search. For example, it is easy to find a *Saccharomyces cerevisiae* gene that encodes pyruvate kinase by searching GenBank using "*Saccharomyces*" and "pyruvate kinase" as keywords in a search. Such a search was done, and two genes were found, CDC19 (also known as PYK1) and PYK2, both coding for a pyruvate kinase.

In brief, this invention provides a subtractive or additive genomic analysis for identifying novel gene mutations that confer desirable phenotypes to industrially useful microorganism without going through the labor-intensive process of metabolic evolution. In this way industrial microbial organisms can be constructed entirely using a rational design. Although this disclosure describes in detail the production of organic acids using microorganisms, and more particularly the production of succinic acid using biocatalysts, a person skilled in the field of industrial microbiology would be able to apply the methods disclosed herein to improve the productivity of other industrial chemicals using a wide variety of microbial biocatalysts.

Experimental Section

General Remarks

Strains, Media and Growth Conditions

New derivatives of *E. coli* C (ATCC 8739) were developed for succinate production using a unique combination of gene deletions coupled with growth-based selection.

The microbial organism of the present invention can be grown in a number of different culture media well known in the field of microbiology. For example, the wild type and mutant strains of *E. coli* are grown in Luria-Bertani (LB) medium containing 1% (w/v) tryptone, 0.5% (w/v) yeast extract, and 0.5% (w/v) NaCl. For the commercial production of the organic acid using fermentative process involving genetically modified microorganism as biocatalyst, a minimal mineral salt medium supplemented with a carbon source is preferred. The use of a minimal mineral salt medium as opposed to a rich medium like LB medium reduces the cost for the production of organic acids in a commercial scale.

The minimal mineral mediums suitable for the present invention include NBS medium (Causey et al., 2007) and AM1 medium (Martinez et al., 2007). The NBS medium contains 1 mM betaine, 25.72 mM $KH_2PO_4$, 28.71 mM $K_2HPO_4$, 26.50 mM $(NH_4)2HPO_4$, 1 mM $MgSO_4.7H_2O$, 0.1 mM $CaCl_2.2H_2O$, 0.15 mM Thiamine HCl, 5.92 µM $FeCl_3 6H_2O$, 0.84 µM $COCl_2.6H_2O$, 0.59 µM $CuCl_2. 2H_2O$, 1.47 µM $ZnCl_2$, 0.83 µM $Na_2MoO_4\ 2H_2O$, and 0.81 µM H$_3$BO$_3$. The AM1 medium contains 1 mM betaine, 19.92 mM (NH$_4$)2HPO$_4$, 7.56 mM NH$_4$H$_2$PO$_4$, 1.5 mM MgSO$_4$.7H$_2$O, 1.0 mM Betaine-KCl, 8.88 µM FeCl$_3$6H$_2$O, 1.26 µM COCl$_2$.6H$_2$O, 0.88 µM CuCl$_2$.2H$_2$O, 2.20 µM ZnCl$_2$, 1.24 µM Na$_2$MoO$_4$2H$_2$O, 1.21 µM H$_3$BO$_3$ and 2.50 µM MnCl$_2$.4H$_2$O. The trace elements are prepared as a 1000× stock and contained the following components: 1.6 g/L FeCl$_3$, 0.2 g/L CoCl$_2$.6H$_2$O, 0.1 g/L CuCl$_2$, 0.2 g/L ZnCl$_2$.4H$_2$O, 0.2 g/L NaMoO$_4$, 0.05 g/L H$_3$BO$_3$, and 0.33 g/L MnCl$_2$.4H$_2$O.

The mineral medium for microbial production of organic acid is supplemented with a carbon source. The carbon sources useful in the present invention include but are not limited to pentose sugars like xylose, hexose sugars like glucose, fructose, and galactose, or disaccharides like sucrose and maltose. The carbon source can also be satisfied by providing a combination of different sugars such as a combination of glucose and xylose. The carbon source can also be derived from a hydrolysis of starch or lignocellulose. The hydrolysis of complex carbohydrates such as starch and lignocelluloses can be achieved either by using thermochemical conversion processes or enzymatic methods well known in the art. The preferred carbon source for the industrial production of organic acid using microbial fermentation is lignocellulosic hydrolysate derived from the hydrolysis of agricultural or forestry wastes. The lignocellulosic hydrolysate may further be fractionated to yield a hexose-enriched and a pentose-enriched fraction and those fractions can serve as the source of carbon for the commercial production of the organic acids using microbial fermentation process. The lignocellulosic hydrolysate can further be detoxified to remove certain chemicals such as furfural which are found to be toxic to a number of microbial organisms above certain concentrations.

During strain construction, cultures were grown aerobically at 30, 37, or 39° C. in Luria broth (10 g l$^{-1}$ Difco tryptone, 5 g l$^{-1}$ Difcoyeast extract and 5 g l$^{-1}$ NaCl) containing 2% (w/v) glucose or 5% (w/v) arabinose. No genes encoding antibiotic resistance, plasmids, or foreign genes are present in the final strains developed for succinate production. However, during the early stages of construction of the different strains, various antibiotic resistance markers were used. The antibiotics such as ampicillin (50 mg l$^{-1}$), kanamycin (50 mg l$^{-1}$), or chloramphenicol (40 mg l$^{-1}$) were added as needed for antibiotic selection process.

Seed cultures and fermentations were grown at 37° C., 100 rpm in NBS or AM1 mineral salts medium containing glucose, 100 mM KHCO$_3$ and 1 mM betaine HCl. In some experiments, corn steep liquor was used. It is a byproduct from the corn wet-milling industry. When compared to the yeast extract and peptone, it is an inexpensive source of vitamins and trace elements.

For fermentative succinate production, strains were grown without antibiotics at 37° C. in NBS mineral salts medium (Causey et al., 2004) supplemented with 10% (w/v) glucose and 100 mM potassium bicarbonate unless stated otherwise. Pre-inocula for fermentation were grown by transferring fresh colonies into a 250 ml flask (100 ml NBS medium, 2% glucose). After 16 h (37° C., 120 rpm), this culture was diluted into a small fermentation vessel containing 300 ml NBS medium (10% glucose, 100 mM potassium bicarbonate) to provide an inoculum of 0.033 g cell dry wt (CDW) l$^{-1}$.

Since the accumulation of organic acids in the growth medium tends to decrease the pH of the medium, it is necessary to add appropriate neutralizing agents as required to the culture medium. The pH of the culture vessel can be continuously monitored using a pH probe, and appropriate base can be added to maintain the pH of the growth medium around neutral pH. The bases suitable for maintaining the pH of the microbial culture includes, but not limited to, NaOH, KOH, NH$_4$SO$_4$, Na$_2$CO$_3$, NaHCO$_3$, and NH$_4$CO$_3$. The bases suitable for this purpose can be used alone or in combination.

In certain experiments, fermentations were automatically maintained at pH 7.0 by adding base containing additional CO$_2$ (2.4 M potassium carbonate in 1.2 M potassium hydroxide). Subsequently, pH was maintained by adding a 1:1 mixture of 3M K$_2$CO$_3$ and 6N KOH. Fermentation vessels were sealed except for a 16 gauge needle which served as a vent for sample removal. Anaerobiosis was rapidly achieved during growth with added bicarbonate serving to ensure an atmosphere of CO$_2$.

Cell growth: Cell mass was estimated by measuring the optical density at 550 nm (OD$_{550}$) using a Thermo Electronic Spectronic 20 spectrophotometer.

Organic acid and sugar analysis: The concentration of various organic acids and sugars were measured by HPLC. Succinic acid and other organic acids present in the fermentation broth were analyzed on Agilent 1200 HPLC apparatus with BioRad Aminex HPX-87H column. BioRad Microguard Cation H$^+$ was used as a guard column. The standards for HPLC analysis were prepared in 0.008N sulfuric acid. The HPLC column temperature was maintained at 50° C. Sulfuric acid at 0.008N concentration was used as a mobile phase at the flow rate of 0.6 ml/min. Quantification of various components was done by measuring their absorption at 210 nm.

EXAMPLES

Example 1

Comparison of the Genome Sequence of KJ122 and E. Coli C Wild Type (ATCC 8739)

KJ122 strain was derived from E. coli C strain through a series of genetic manipulations and a number or rounds of metabolic evolution. The details of the construction of KJ122 strain are provided in the published PCT Patent Applications Nos. WO/2008/15958 and WO/2010/115067 which are incorporated herein by reference. Two scientific publications by Jantama et at (2008a and 2008b) and two scientific publication by Zhang et al (2009a; 2009b) also describe the construction of KJ122 strain. Both these scientific publications are incorporated herein by reference. Strain KJ122 has been deposited at the USDA-ARS culture collection on Feb. 20, 2008 with strain designation number B-50115.

The genomic sequence of KJ122 and was obtained using an Illumina sequencing system at the Tufts University Core Facility, and the sequence was compared to the annotated wild type E. coli C sequence that is available from GenBank (Acession number CP000946). From this comparative genome analysis, a number of genetic differences between these two strains were detected. In this disclosure, the location of mutations that occur in an open reading frame will be given using coordinates based on the number of the nucleotide base, counting the first base of the start codon of the open reading frame (as annotated in the GenBank sequence referenced above) as base number one. From a list of genetic difference between the KJ122 and E. coli C, the deletions that had been intentionally introduced at various stages in the construction KJ122 were verified, and an additional list of genetic changes that occurred during the process of metabolic evolution were identified. Included in the list of mutations that were fixed in the genome of KJ122 during the process of metabolic evolution were 1) a frameshift mutation in pykA (SEQ ID NO. 1), which encodes one of two pyruvate kinases, 2) a frameshift mutation in the galS gene (SEQ ID NO. 2), which encodes a repressor of galactose inducible genes, such as the sugar transporter gene galP, 3) a 48 kilobase deletion (SEQ ID NO. 3) of a region of the *E. coli* genome comprising many genes including ydcC through ydcF of the *E. coli* C genome, 4) A point missense mutation in the C-terminal domain of the rpoA gene (SEQ ID NO. 4), which encodes a subunit of RNA polymerase, 5) a point missense mutation in the F region of the rpoC gene (SEQ ID NO. 5), which encodes a different subunit of RNA polymerase, 6) a frameshift mutation in the gldA gene (SEQ ID NO. 6), which encodes glycerol dehydrogenase, 7) a frameshift mutation in the dhaM gene (SEQ ID NO. 7, which encodes a subunit of a PEP-dependent dihydroxyacetone kinase, and 8) a missense point mutation in the ftsI gene (SEQ ID NO. 8), which encodes a gene involved in cell wall synthesis and cell shape.

Example 2

Curing the Mutated pykA Gene in KJ122

When wild type *E. coli* and many other bacteria are grown in glucose containing medium, pyruvate production inside the cell occurs through the action of the phosphotransferase system (PTS), which uses a molecule of phosphoenolpyruvate (PEP) to transport and phosphorylate glucose with the resulting formation of a molecule of pyruvate. Pyruvate formation can also occur from the action of pyruvate kinase enzyme coded by the pykA and/or pykF genes. PykA and PykF proteins are isoenzymes. When glucose is the source of carbon, both pyruvate kinases isoenzymes have an active role in pyruvate biosynthesis. However, a triple mutant, pts, pykA and pykF is incapable of growing on glucose as a sole carbon source, since the cell's ability to form pyruvate is absent or greatly diminished (Ponce et al., 1995).

Since KJ122 contains a mutation in ptsI coding for the protein PtsI, which is a component of the PTS (Zhang et al., 2009a Zhang et al., 2009b), the observation that the pykA gene had also been mutated in KJ122 during the metabolic evolution was unexpected. In order to determine whether this mutation contributes toward succinic acid production, the wild type pykA allele was installed in KJ122 to give new strain WG85a, and the phenotypic changes in terms of the effect of this mutation on succinic acid production were assessed. WG85a was constructed in two steps using the two step gene replacement method described above. In the first step, a cat-sacB cassette was installed at the pykA locus of strain KJ122 to give strain WG84. The PCR primers used were SEQ ID NO. 21 and 22 (see Table 1). In the second step, the wild type pykA gene from *E. coli* C was installed into WG84 to give strain WG85a. The PCR primers used were SEQ ID NO. 23 and 24 (see Table 1). WG85a produced about 160 mM succinate compared to about 550 mM for KJ122. Clearly the pykA mutation in KJ122 is important for succinate production. Since the pykA mutation in KJ122 is a frameshift, it can be deduced that a strain containing a deletion of pykA should perform similarly. The intermediate strain, WG84, contains a complete deletion of the pykA open reading frame, and as predicted, WG84 performed similarly to KJ122 with a succinate titer of 540 mM, showing that the frameshift mutation in KJ122 is similar to a null mutation. Having made this discovery, the inventors could then deduce that a reduced level of pyruvate kinase activity is important for KJ122, and that this state could be achieved by any one of a number of related approaches. For example, the ptsI* activity in KJ122 could be further reduced or eliminated, PykF activity could be diminished or eliminated, or a combination of decreased activity of PykA, PykF, and/or PtsI could be used to establish a reduction in the total pyruvate kinase activity that is now known to be important for succinate production.

In order to determine whether a deletion in the second pyruvate kinase gene, pykF, could substitute for a deletion in pykA, a deletion in pykF was installed into strain WG85a, to give strain WG89. This was accomplished using the two step gene replacement method. For the first step, a kan-sacB cassette was installed at the pykF locus of WG85a, to give strain WG87. The primers used were SEQ ID NO. 36 and 37 (see Table 1). For the second step, a deletion of the pykF open reading frame was installed in WG87 to give new strain WG89. The PCR primers used were SEQ ID NO. 38 and 39 (see Table 1), and the template was pGW191 (SEQ ID NO 35). In small scale fermentors, WG89 grew more poorly and produced only 115 mM succinate, compared to 510 mM for KJ122. Thus, a deletion of pykF cannot substitute for a deletion or frameshift of pykA for improving succinate production. Although WG89 and WG85a were tested in different experiments, it appears that WG89 performed more poorly than WG85a, showing that there is an optimum level of pyruvate kinase for growth and succinate production in KJ122, but that deletion of pykF results in a level of total pyruvate kinase activity that is not optimal for good succinate production. Thus, metabolic evolution has produced a strain that has a level of pyruvate kinase that is close to the optimal level. Moreover, a deletion of all genes that encode pyruvate kinase (pykA, pykF, and one or more pts genes), as suggested in the U.S. Patent Application Publication 2009/0075352 and Lee et al. (2005) would not improve succinate production, because the total pyruvate kinase activity would be too low in such a strain. When constructing a new succinate production strain in a new strain, for example in *Saccharomyces cerevisiae*, according to the present invention, after blocking unwanted pathways, the level of total pyruvate kinase would be adjusted to give a good efficiency of succinate production. This can be accomplished, for example, by deleting PYK2, the nonessential pyruvate kinase gene, and then varying the level of expression or activity of the remaining PYK1, by installing promoters of varying strength in front of PYK1, or by making progressive deletions from the 5' end or 3' end of the PYK1 open reading frame, and testing for improved succinate production.

Example 3

Mutating galS in XZ722

Comparative genome sequence analysis between *E. coli* C strain and KJ122 strain revealed a frameshift mutation in the galS gene. This gene is known to repress the expression of galP gene encoding a galactose permease, GalP. GalP protein is reported to be at least partly responsible in the absence of a fully functional phosphotransferase system (PTS) for glucose transport, as is the case in KJ122 strain in which the ptsI coding for PtsI protein, a component of PTS is mutated (Zhang et al 2009a). Thus it is possible that galS mutation in KJ122 has some functional significance in terms of glucose uptake or some other effect on the rate of succinic production. This is tested by transferring the KJ122 allele of galS into *E. coli* strain XZ722 (ΔpflBB, ptsI*, pck*) to give new strain WG86a and assessing the effect of the mutation on the rate of succinic acid production in this strain. WG86a was constructed in two steps using the two step gene replacement method described above. In the first step, a kan-sacB cassette was installed at the galS locus of strain XZ722 to give strain WG83. The PCR primers used were SEQ ID NO. 17 and 18 (see Table 1). In the second step, the frameshifted allele of galS from KJ122 gene was installed to give strain WG86a. The PCR primers used were SEQ ID NO. 19 and 20 (see Table 1). In small scale fermentors, the succinate titer from XZ722 was 175 mM, while that of WG86a was 210 mM, proving that the galS mutation can contribute to improved succinate production. The galS mutation is a frameshift, so it can be deduced that a deletion in galS would behave similarly, but would be more stable genetically. Intermediate strain WG83 contains a deletion of the galS open reading frame, and it behaved similarly to WG86a, producing 220 mM succinate. In addition, the inventors can deduce that mutating the galR gene, which is known to encode a different repressor of galP expression, would also enhance succinic acid production by increasing the cell's ability to import glucose. Furthermore, the inventors can deduce that an increase in copy number of the galP gene would have a similar effect and offer yet another approach to increasing efficiency of succinate production. The galP gene and adjacent upstream and downstream DNA containing a promoter and terminator, with or without regulatory sites, can be amplified by PCR and then installed in the chromosome of a succinate producing *E. coli* strain at one or more sites that are distant from the native galP locus, to give a strain containing more than one copy of the galP gene. The resulting strain will be enhanced for succinic acid production by virtue of having a higher level of GalP protein (see Example 11).

Example 4

Deleting a 48 kbp Region from Chromosomal DNA

Comparative genome sequence analysis between KJ122 and *E. coli* C strains has revealed the deletion of a 48 kilobase region including genes ydcC through ydcF of the genome in KJ122 during the process of metabolic evolution. This deletion corresponds to the sequence between nucleotide coordinates 2,416,108 and 2,464,284 (both nucleotides inclusive) of *E. coli* ATCC 8739. The functional significance of this gene deletion and its impact on succinic acid production is assessed by reinstalling the 48 kilobase sequence in KJ122 to give strain WG110. This is accomplished in two steps using a combination of the gene replacement method and P1 vir transduction. For the first step, a cat-sacB cassette was installed between the deletion endpoints of KJ122 to give strain WG51. The PCR primers used were SEQ ID NO, 31 and 32 (see Table 1). In the second step, WG51 is transduced to sucrose resistance and chloramphenicol sensitivity, using P1 vir with *E. coli* C as the donor, to give new strain WG110, which now has the 48 kilobase sequence reinstated at its native locus in a KJ122 strain background. Deletion of the specific regions of strains of *E. coli* can be accomplished using the methods described in the U.S. Patent Applications Publications 2009/0075333 and 2008/0009041. The specific 48 kilobase deletion of KJ122 can be installed in other recipient *E. coli* strains in two steps by (1) transducing from WG51 into the recipient strain, selecting for chloramphenicol resistance, and (2) transducing from KJ122 into the strain constructed in step one, selecting for sucrose resistance, and screening for chloramphenicol sensitivity.

Obviously, the genes contained under the 48 kilobase deletion are not essential for growth in minimal glucose medium or for succinic acid production. The advantage of the 48 kb deletion is that the resulting chromosome is slightly shorter, which will give a slight increase in the rate of growth. Moreover, there are at least four genes under the deletion, which when deleted singly, result in a higher density of growth in minimal glucose medium. Strains JW5226, JW1427, JW5229, and JW1438 of the Keio deletion collection, which contain deletions in genes ydcI, ydcL, ydcO, and ydcV, respectively, all grow to significantly higher OD600 at 48 hours in a minimal glucose medium (see Supplementary Table 3. in Baba, T. et. al (2006).

Example 5

Curing the Mutated rpoA Gene in KJ122

The core enzyme of bacterial RNA polymerase contains four different polypeptide subunits: alpha ($\alpha$), beta ($\beta$), beta' ($\beta'$) and omega ($\omega$) in the stoichiometry $\alpha_2\beta\beta'\omega$. The alpha subunit of RNA polymerase is coded by rpoA gene. This subunit is required for assembly of the enzyme and it interacts with some regulatory proteins. Comparative genome sequence analysis between KJ122 and *E. coli* C strains revealed a missense point mutation in the rpoA gene. More specifically, this mutation is located at amino acid position 322 in the RNA polymerase alpha subunit C-terminal domain ($\alpha$-CTD). The proline residue in the wild type *E. coli* C strain has been converted into a leucine residue in the KJ122 strain.

A different mutation that changes proline 322 to alanine has been previously described as having a negative effect on expression of the metE gene (Fritsch et al., 2000). In a separate report, a proline to alalnine mutation at this position in the RpoA protein was found to reduce cyclic AMP receptor protein (CRP) activation of the rhaS promoter in *E. coli* (Holcroft and Egan, 2000). The effect of the proline to leucine point mutation in the RpoA protein of KJ122 was assessed by transferring the wild type allele of rpoA mutation into KJ122 to give new strain RY859A1, and determining the effect of this mutation on succinic acid production. RY859A1 was constructed in two steps using P1 vir transduction. First, a linked aroE::kan allele was transduced into KJ122 using JW3242 from the Keio deletion collection (available from the Coli Genetic Stock Center, Yale University, New Haven, Conn., USA) as the donor, and selecting for kanamycin resistance. For the second step, wild type *E. coli* C was used as the donor, and selection was for growth on minimal glucose medium. The sequence of the rpoA gene of RY859A1 was determined and shown to be wild type. In small scale fermentors at 48 hours, RY859A1 produced succinate at 370 mM, which was slightly less than KJ122, which produced 385 mM. The fermentations were performed in duplicate and were reproducible.

Example 6

Curing the Mutated rpoC Gene in KJ122

Comparative genome sequence analysis between KJ122 and *E. coli* C strain revealed a missense point mutation in the F region of $\beta'$ subunit of RNA polymerase coded by the rpoC gene. The RpoC protein binds to the DNA template during the RNA synthesis. A methionine residue at position 747 has been replaced with isoleucine in KJ122. The effect of this point mutation in the RpoC protein of KJ122 was assessed by transferring the wild type allele of rpoC mutation into KJ122 to give new strain RY862A, and determining the effect of this mutation on succinic acid production. RY862A was constructed using P1 vir transduction. A linked thiG::kan allele was transduced into KJ122 using JW5549 from the Keio deletion collection (available from the Coli Genetic Stock Center, Yale University, New Haven, Conn., USA) as the donor, and selecting for kanamycin resistance. The sequence of the rpoC gene of RY862A was determined and shown to be wild type. Thiamine HCl at 5 mg/liter was added to the fermentation medium for RY862A and control KJ122 to insure growth of RY862A. In small scale fermentors, at 48 hours, the succinate titer of RY862A was 320 mM, significantly less than that of KJ122, 425 mM. The initial growth rate of RY862A was also slower than that of KJ122, 0.15 OD550/hr compared to 0.23 OD550/hr. The fermentations were performed in duplicate and were reproducible.

Example 7

Curing the Mutated gldA Gene in KJ122

The NAD$^+$-dependent glycerol dehydrogenase is encoded by the gldA gene. GldA protein catalyzes the reversible oxidation of glycerol to dihyrdroxyacetone, and can also catalyze the reduction of methylgloxal to R-Lactaldehyde. Comparative genome sequence analysis has revealed that the gldA gene in KJ122 contains a frameshift mutation. The impact of the mutated form of the gldA gene on succinic acid production was assessed by installing the wild type gldA gene into KJ122, using the two step gene replacement method described above, to give new strain AC6. In the first step, a cat-sacB cassette was installed at the gldA locus of strain KJ122 to give strain AC5. The PCR primers used were SEQ ID NO. 9 and 10 (see Table 1). In the second step, the wild type gldA gene from *E. coli* C was installed into AC5 to give strain AC6. The PCR primers used were SEQ ID NO. 13 and 14 (see Table 1). In small scale fermentors at 96 hours, the succinate titer of AC6 was 580 mM, slightly higher than that of KJ122, which was 530 mM. However, the initial growth rate of AC6 was 0.16 OD550/hr, slightly slower than that of KJ122, which was 0.20 OD550/hr. Thus, the mutated gldA gives a slight growth advantage that would be selected for during the metabolic evolution of KJ122.

Example 8

Curing the Mutated dhaM Gene in KJ122

Dihydroxyacetone kinase is a multisubunit protein related to the phosphotransferase (PTS) system, encoded by three genes in one operon, dhaKLM. The DhaM subunit has sequence similarity to the IIA domain of the mannose transporter, the phosphoryl carrier protein Hpr and the N-terminal domain of enzyme 1. In *E. coli*, DhaM uses PEP instead of ATP as the donor for phosphate in the phosphorylation of dihydroxyacetone. DhaM is phosphorylated by PEP through enzyme 1 and the phosphoryl carrier protein HPr. The dhaM gene of KJ122 contains a frameshift mutation. In order to assess the effect of the dhaM mutation in KJ122, the wild type dhaM gene was installed in KJ122 using the two step gene replacement method described above to give new strain AC2. In the first step, a cat-sacB cassette was installed at the dhaM locus of strain KJ122 to give strain AC1. The PCR primers used were SEQ ID NO. 11 and 12 (see Table 1). In the second step, the wild type dhaM gene from *E. coli* C was installed in AC1 to give strain AC2. The PCR primers used were SEQ ID NO. 15 and 16 (see Table 1). In small scale fermentors, at 96 hours, the titer of succinate from AC2 was 560 mM, slightly higher than that of KJ122, 530 mM. However, the initial growth rate of AC6 was 0.16 OG550/hr, slightly slower than that of KJ122, which was 0.20 OD550/hr. Thus, mutating dhaM gives a slight growth advantage that would be selected for during the metabolic evolution of KJ122. Since DhaKLM consumes PEP, which is a substrate for succinic acid biosynthesis, conservation of PEP is a mechanism for the growth advantage of KJ122. In addition to, or instead of, mutating the genes in the dhaKLM operon, a gene encoding a subunit of any other PTS-dependent dihydroxyacetone kinase can also be mutated to test their importance in succinic acid production.

Example 9

Curing the Missense Mutation in the ftsI Gene in KJ122

The ftsI gene encodes an essential protein involved in cell wall synthesis and/or septation. The ftsI gene of KJ122 contains a missense mutation that changes base 619 of the coding sequence from a C to a T, which changes arginine 207 to a cysteine. The effect of the arginine to cysteine point mutation in the FtsI protein of KJ122 was assessed by transferring the wild type allele of ftsI mutation into KJ122 to give new strain RY858G1, and determining the effect of this mutation on succinic acid production. Since FtsI is an essential protein, the two step gene replacement method would not work, so a two step P1 vir transduction was used instead to construct RY858G1. First, a linked leuA::kan allele was transduced into KJ122 using JW0073 from the Keio deletion collection (available from the Coli Genetic Stock Center, Yale University, New Haven, Conn., USA) as the donor, and selecting for kanamycin resistance, to give new strain RY853G1. For the second step, *E. coli* C was used as the donor, RY853G1 was the recipient, and selection was for growth on minimal glucose medium. The sequence of the ftsI gene of RY858G1 was determined and shown to be wild type. In small scale fermentors, RY858G1 grew at about the same initial rate as KJ122, but at 72 hours, RY858G1 produced slightly less succinate, 440 mM, than KJ122, which produced 460 mM. Thus the missense mutation in the ftsI gene of KJ122 contributes slightly to an increase in succinate titer.

Example 10

Additive Effect of Combining Mutations

The results of the strain comparisons that were described in detail in the above examples are summarized in Table 3. Many of the mutations that have been tested one at a time gave only a slight increase in succinate titer or growth rate. However, these increases must be additive and/or synergistic to give the overall improvement that was found for KJ122 relative to its ancestors (Jantama et al., 2008a; Jantama et al 2008b). For example, a derivative of KJ122 cured for both the missense mutation in rpoA and the missense mutation in rpoC, constructed by transducing the wild-type rpoC gene into RY859A1, which contains wild-type rpoA gene, resulted in a new strain, RY860A. The construction of RY860A was done in the same way as RY862A described above in Example 6, except that the recipient strain was RY859A1 instead of KJ122. In small scale fermentors at 48 hours with a supplement of thiamine HCl at 5 mg/l, RY860A produced significantly less succinate (300 mM) than KJ122 (425 mM) and less than RY862A (320 mM) that was cured for only the rpoC mutation.

Example 11

Construction of a New Succinate Producer from a Naïve Strain

Strain TG128 is a D-lactate producer that was derived from *E. coli* W (ATCC 9637), with a genotype ΔfrdABCD, ΔadhE, ΔpflB, ΔmgsA, and Δack. TG128 has been deposited with the Agricultural Research Services Culture Collection, 1815 N. University Street, Peoria, Ill., 61604 U.S.A. on Jul. 25, 2005 and has strain accession number NRRL B-30962. TG128 was then metabolically evolved by selecting first for growth on sucrose, second for growth at 39 degrees centigrade, and third for growth at 40 degrees centigrade. The resulting strain was named TG160. TG160 was then re-engineered to be a succinic acid producing strain. Alleles from KJ122 were installed in the following chronological order, using the two step gene replacement method described above: pck*, ΔldhA, frd-ABCD$^+$, and ptsI*. The pck* and ptsI* mutations were both mutations that had been found in the KJ122 genome and that had been shown to increase efficiency of succinic acid production (Zhang et al., 2009a). The resulting strain, WG32b, was then grown in a small microaerobic fermentors for about 126 generations (23 transfers), to give strain WG32b-T23. WG32b-T23 is a moderately good succinic acid producer that made about 260 mM succinic acid in small scale fermentors. Next, two additional mutations were added to WG32b-T23, based on discoveries of the present invention in the genome of KJ122. First, a second copy of the galP gene, together with flanking sequences containing the native promoter and terminator, was integrated in the genome at a locus near the dnaA gene, using the two step gene replacement method. The DNA sequence at the insertion site is: attaaattttccaatatgcggcg-taaatcgtgcccgcctcgcggcag-gatcgtttacacttagcgagttctggaaagtcctgtggataa atcgggaaaatctgt-gagaaacagaagatct—insertion site—cttgcgcagtttaggctatgatccgcggtcccgatcgttttgcaggatcttgactc-gggcatataaccgcagacagcggt. In the first step, a kan-sacB cassette was inserted at the dnaA locus to give strain WG62. The PCR primers used were SEQ ID NO. 25 and 26 (see Table 1). In the second step, the second copy of galP was installed at the dnaA locus. The PCR primers used were SEQ ID NO. 27 and 28 (see Table 1). The resulting strain, named WG74, produced about 320 mM succinic acid in small scale fermentations. Second, the entire open reading frame of the pykA gene was deleted from WG74 and replaced with a cat-sacB cassette to give new strain WG96. The PCR primers used were SEQ ID NO. 29 and 30 (see Table 1). In small scale fermentations, WG96 produced 450 mM succinic acid, which is a clear improvement over that of precursor strains WG32b-T23 and WG74. Thus, the inventors have clearly established that discovering the exact nature of the mutations in KJ122 gives unique information and insight into how to construct new, improved succinic acid producing strains from different, less evolved parent strains. Moreover, the discoveries of the present invention are applicable broadly. For example, learning of the galS mutation can be applied by not only installing the identical mutation found in KJ122 in a new strain, but also by duplicating a target of GalS repression, the galP gene. As another example, learning of the pykA mutation can be applied by not only installing the identical mutation found in KJ122 in a new strain, but also by installing a deletion of pykA.

The invention disclosed herein can be generalized to improving strains and processes for producing chemicals other than succinic acid. The examples provided are intended to be illustrative, but not limiting.

The GalP protein functions to import glucose and other sugars by a proton symport mechanism, which costs the cell roughly ⅓ of an ATP. After importation, a sugar such as glucose needs to be phosphorylated, which costs one additional ATP, for a total cost of about 1.33 ATPs. In terms of metabolic energy, this is less costly than importing a sugar such as glucose by the PTS system, which costs one PEP, which is energetically equivalent to about 2 ATPs. Thus, importing a sugar such as glucose by GalP is more efficient than by using the PTS.

Moreover, in many fermentative processes, particularly, but limited to anaerobic and microaerobic processes, PEP can an intermediate for biosynthesis of chemicals other than succinic acid, such as malic acid, fumaric acid, aspartate, threonine, methionine, lysine, and others. Thus, conserving PEP by using GalP instead of the PTS, and by reducing pyruvate kinase activity in general, the efficiency of biosynthesis can be improved.

In many fermentations, more efficient growth in minimal media is desirable, and the 48 kb deletion found in KJ122 will help improve efficiency in any fermentation using E. coli in minimal medium.

The ftsI mutation found in KJ122 might improve efficiency by leading to a smaller or more spherical cell, which in turn leads to a higher surface area to volume ratio. This, in turn, will lead to more efficient import of nutrients such as glucose, sucrose, maltose, glycerol, etc., and more efficient export of products such as succinate, malate, fumarate, aspartate, threonine, methionine, lysine, etc.

The mutations found in rpoA and rpoC result in a general loss of catabolite repression by glucose. This de-repression increases efficiency of biosynthesis in many cases. For example, biomass hyrolyzates, which are desirable sources of inexpensive sugars, usually contain mixtures of sugars including glucose. It is desirable that the various other sugars be used simultaneously with the glucose, and removal of catabolite repression enhances the cell's ability to efficiently consume and metabolize non-glucose sugars together with glucose. Furthermore, removal of catabolite repression increases expression of desired genes, such as pck, galP, mdh, fumA, xylE, lacZ, lacY, fumB, and frdABCD. Thus the RNA polymerase mutations of the invention have broad applicability to a variety of commercial useful strains and fermentation processes.

Thus, the mutations discovered in the present invention are useful for increasing succinic acid production, they are novel in that they have not been previously described for succinic acid production or other organic acid production, and they are inventive in that one skilled in the art could not have predicted that the individual mutations of the inventions or the combination of those mutations would improve succinic acid or other organic acid production.

Although several of the mutations discovered by in the genome sequence of KJ122 produced only a slight effect on growth or succinic acid production when altered one at a time, it should be stressed that even a small increase in rate of growth would be selected for during the metabolic evolution, as the time period covered many generations. Moreover, a combination of several mutations, in which each individual mutation contributes additively or synergistically would confer a much larger increase in efficiency of growth and/or succinic acid production.

The method for constructing a microorganism for the purpose of producing a desired chemical by fermentation from a new, second parent strain, as disclosed in Example 11, can be generalized to a wide variety of chemicals and strains. The general method would comprise: (A) deleting from a first parent strain at least one gene encoding an enzyme that catalyzes a step in a biosynthetic pathway to a fermentation product distinct from said desired chemical, to result in a first intermediate strain, (B) performing metabolic evolution on said first intermediate strain to result in a second intermediate strain, (C) determining the genomic DNA sequence of said parent strain and said second intermediate strain, (D) comparing said genomic DNA sequences to identify mutations that were selected for during said metabolic evolution, (E) testing at least one of said mutations to determine which of said mutations are beneficial for increasing the growth rate or efficiency of production of said desired chemical, (F) choosing at least one of said beneficial mutations, and (G) installing at least one of said beneficial mutations, or at least one mutations that is functionally similar to one of said beneficial mutations, in a second parent strain to result in said microorganism.

This general method will apply to chemicals other than succinate, such as fumarate, malate, aspartate, glutamate, and derivatives of any of these chemicals, and to microorganisms other than *E. coli*, including other bacteria, archeons, yeasts, filamentous fungi, algae, and dinoflagellates.

The applicants' invention has been described in detail above with particular reference to preferred embodiments. A skilled practitioner familiar with the above detailed description can make any modification without departing from the spirit of the claims that follow.

TABLE 1

Sequences of the primers used

| SEQ ID NO. | Primer name | Sequence (5' > 3') |
|---|---|---|
| 9 | BY60 | caggaaacgctgaccgtactggtcggctaccagcagagcggcgtaaacctgtgacggaagatcacttcgcagaataa |
| 10 | BY61 | gtgagtttgaccgctatctgctgttgccaaataacccgaatatggtcattgaagcacttcactgacaccctcatca |
| 11 | BY62 | tctctggcggtggtcataaaaaaccgtaacggcctgcatgtacgtccggcgtgacggaagatcacttcgcagaataaaat |
| 12 | BY63 | aaccctgacggttgaaacgttgcgttttaacgtccagcgttagcgtttctgaagcacttcactgacaccctcatca |
| 13 | AC16 | gcattgtctgttatctacaccgatgagg |
| 14 | AC17 | tcccactcttgcaggaaacgct |
| 15 | AC33 | gactgggagaaggtgtcggtgaat |
| 16 | AC34 | catcattaaacagcggccctaataaaata |
| 17 | 91A | aaacgccaatgcccaggcgctggcaactcaggttagcgacaccattggcgtggtggtgatctagcgcatgcatccattta |
| 18 | 91B | aatcaacgcattacaacgctggcgaattaacacctcaatggcgtgacgctcttttccgcggcgaagaactccagcatga |
| 19 | 90A | gaataacagcacgctggtca |
| 20 | 90B | tcaacgcactcatccagcct |
| 21 | 60A | atgtccagaaggcttcgcagaacaaaaatcgttaccacgttaggcccagcaacagatcgcgacggaagatcacttcgcag |
| 22 | 60B | ttactctaccgttaaaatacgcgtggtattagtagaacccacggtactcatcacgtcgccaagaaataaaagaaaatgcc |
| 23 | 59A | tacatgtccagaaggcttcg |
| 24 | 59B | catccggcaacgtacttact |
| 25 | 75A | ccaggacgatccttgcgctttacccatcagcccgtataatcctccacccggcgcgccatgctagcgcatgcatccattta |
| 26 | 75B | ccgcgcttttccgcaccttttcgcagggaaatgtacgacctcacaccagtggaaaccagcggcgaagaactccagcatga |
| 27 | 76A | ccaggacgatccttgcgctttacccatcagcccgtataatcctccacccggcgcgccatgccgattacaccaaccacaac |
| 28 | 76B | ccgcgcttttccgcaccttttcgcagggaaatgtacgacctcacaccagtggaaaccagc ggcgaatttcatagctttcc |
| 29 | 60A | atgtccagaaggcttcgcagaacaaaaatcgttaccacgttaggcccagcaacagatcgcgacggaagatcacttcgcag |
| 30 | 60B | ttactctaccgttaaaatacgcgtggtattagtagaacccacggtactcatcacgtcgccaagaaataaaagaaaatgcc |
| 31 | 67A | ggctgggacggaagtcgctgtcgttctcaaaatcggtggagctgcatgacaaggtcatcggacggaagatcacttcgcag |
| 32 | 67B | atggagcagattagcggttaaccctgctatttgcctgataaatctaaaacccggtaagcaaagaaataaaagaaatgcc |

TABLE 1-continued

Sequences of the primers used

| SEQ ID NO. | Primer name | Sequence (5' > 3') |
|---|---|---|
| 36 | 87A | atgaaaaagaccaaaattgtttgcaccatcggaccgaaaaccgaatctgaagagatgtctagcgcatgcatccattta |
| 37 | 87B | ttacaggacgtgaacagatgcggtgttagtagtgccgctcggtaccagtgcaccagaaaggcgaagaactccagcatga |
| 38 | 78A | acacattcctctgcacgctt |
| 39 | 78B | aggatgcttccatcggattc |

TABLE 2

Primers pairs and DNA template used and the bacterial strains created

| PCR Primer pair | DNA template | Strain Created |
|---|---|---|
| BY60/BY61 | pCA2 | AC5 |
| BY62/BY63 | pCA2 | AC1 |
| AC16/AC17 | E. Coli C | AC6 |
| AC33/AC34 | E. Coli C | AC2 |
| 91A/91B | pGW162 | WG83 |
| 90A/90B | KJ122 | WG86 |
| 60A/60B | pLOI4151 | WG84 |
| 59A/59B | E. coli C | WG85 |
| 75A/75B | pGW162 | WG62 |
| 76A/76B | KJ122 | WG74 |
| 60A/60B | pLOI4151 | WG96 |
| 67A/67A | pLOI4151 | WG51 |
| 87A/87B | pGW162 | WG87 |
| 78A/78B | pGW191 | WG89 |

TABLE 3

Details of the mutations detected through whole genome sequencing

| Relevant gene(s) | Strain name | Parent strain | Allele type | Succinate titer | Initial growth rate OD550/hr | Fermentation time (hr) for titer given |
|---|---|---|---|---|---|---|
| pykA | KJ122 | — | frameshift | 550 mM | 0.21 | 96 |
| pykA | WG85a | KJ122 | wild type | 160 mM | 0.022 | 96 |
| pykA | WG84 | KJ122 | deletion | 540 mM | 0.21 | 96 |
| pykA, F | KJ122 | — | pykA$^{fs}$, pykF+ | 510 mM | 0.20 | 97 |
| pykA, F | WG89 | KJ122 | pykA+, ΔpykF | 115 mM | 0.021 | 97 |
| galS | XZ722 | — | wild type | 175 mM | 0.017 | 144 |
| galS | WG86a | XZ722 | frameshift | 210 mM | 0.019 | 144 |
| galS | WG83 | XZ722 | deletion | 220 mM | 0.018 | 144 |
| rpoA | KJ122 | — | missense | 385 mM | 0.24 | 48 |
| rpoA | RY859A1 | KJ122 | wild type | 370 mM | 0.23 | 48 |
| rpoC | KJ122 | — | missense | 425 mM | 0.23 | 48 |
| rpoC | RY862A | KJ122 | wild type | 320 mM | 0.15 | 48 |
| rpoA, rpoC | RY860A | RY859A1 | wild type for both | 300 mM | 0.14 | 48 |
| gldA | KJ122 | — | frameshift | 530 mM | 0.20 | 96 |
| gldA | AC6 | KJ122 | wild type | 580 mM | 0.16 | 96 |
| dhaM | KJ122 | — | frameshift | 530 mM | 0.20 | 96 |
| dhaM | AC2 | KJ122 | wild type | 560 mM | 0.16 | 96 |
| ftsI | KJ122 | — | missense | 460 mM | 0.20 | 72 |
| ftsI | RY858G1 | KJ122 | wild type | 440 mM | 0.20 | 72 |

REFERENCES

All references are listed for the convenience of the reader. Each reference is incorporated by reference in its entirety.

U.S. Pat. No. 6,455,284
U.S. Pat. No. 6,962,794
U.S. Pat. No. 6,989,265
U.S. Pat. No. 7,223,567
U.S. Pat. No. 7,229,794
U.S. Pat. No. 7,303,906
U.S. Pat. No. 7,371,558
U.S. Pat. No. 7,524,660
U.S. Pat. No. 7,629,162
U.S. Patent Application Publication No. 2004/0214294
U.S. Patent Application Publication No. 2004/0146966
U.S. Patent Application Publication No. 2005/0181488
U.S. Patent Application Publication No. 2005/0176114
U.S. Patent Application Publication No. 2005/0221455
U.S. Patent application Publication No. 2006/0073577
U.S. Patent Application Publication No. 2007/0111294
U.S. Patent Application Publication No. 2008/0009041
U.S. Patent Application Publication No. 2008/0176302
U.S. Patent Application Publication No. 2008/0293100
U.S. Patent Application Publication No. 2009/0047719
U.S. Patent Application Publication No. 2009/0075333
U.S. Patent Application Publication No. 2009/0075352
U.S. Patent Application Publication No. 2009/0221055
U.S. Patent Application Publication No. 2009/0325243
U.S. Patent Application Publication No. 2010/0143997
U.S. Patent Application Publication No. 2010/0261239

U.S. Patent Application Publication No. 2010/0248311

U.S. Patent Application Publication No. 2010/0279369

International Patent Application Publication No. WO 2008/115958

International Patent Application Publication No. WO 2010/115067

European Patent Application EP 2,241,630

Altaras, N. E., Cameron, D. C. "Metabolic engineering of a 1,2-propanediol pathway in *Escherichia coli*." *App Environ Microbiol* 65: 1180-1185.

Andersson, C., Hodge, D., Berglund, K. A., Rova, U. "Effect of different carbon sources on the production of succinic acid using metabolically engineered *Escherichia coli*." *Biotechnol Prog* 23: 381-388.

Baba, T., Ara, T., Hasegawa, M., Takai, Y., Okumura, Y., Baba, M., Datseko, K. A., Tomita, M., Wanner, B. L., Mori, H. "Construction of *Escherichia coli* K-12 in-frame, single-gene knockout mutants: the Keio collection." *Mol Syst Biol* 2: Article number: 2006.0008

Babitzke, P., Romeo, T. "CsrB sRNA family; sequestration of RNA-binding regulatory proteins." *Curr Opin Microbiol* 10: 156-163.

Causey, T. B., Shanmugam, K. T., Yomano, L. P, Ingram, L. O. "Engineering *Escherichia coli* for efficient conversion of glucose to pyruvate." *Proc Natl Acad Sci USA* 101:2235-2240.

Cronan, J., Laporte, D. "Tricarboxylic acid cycle and glyoxylate bypass" in *Escherichia Coli* and *Salmonella*." editors Neidhardt, F., et al., ASM Press, Washington, D.C., USA.

Datsenko, K. A., Wanner, B. L. "One-step inactivation of chromosomal genes in *Escherichia coli* K-12 using PCR products." *Proc Natl Acad Sci USA* 97: 6640-6645.

Fritsch, P. S., Urbanowski, M. L., Stauffer, G. V. "Role of RNA polymerase a subunits in MetR-dependent activation of metE and metH: Important residues in the C-terminal domain and orientation requirements within RNA polymerase." *J Bacteriol* 182:5539-5550.

Holcroft, C. C., Egan, S. M. "Interdependence of activation at rhaSR by cyclic AMP receptor protein, the RNA polymerase alpha subunit C-terminal domain, and RhaR." *J Bacteriol* 182: 3529-3535.

Ikeda, M., Ohnishi, J., Hayashi, M., Mitsuhashi, S. "A genome-based approach to create a minimally mutated *Corynebacterium glutamicum* strain for efficient L-lysine production." *J Ind Microbiol Biotechnol* 33: 610-615

Jantama, K., Haupt, M. J., Svoronos, S. A., Zhang, X., Moore, J. C., Shanmugham, K. T., Ingram, L. O. "Combining metabolic engineering and metabolic evolutions to develop nonrecombinant strains of *Escherichia coli* C that produce succinate and malate." *Biotechnol Bioeng* 99: 1140-1153.

Jantama, K., Zhang, X., Moore, J. C., Shanmugam, K. T., Svoronos, S. A., Ingram, L. O. "Eliminating side products and increasing succinate yields in engineered strains of *Escherichia coli* C." *Biotechnol Bioeng* 101: 881-893.

Kurzrock, T., Weuster-Botz, D. "Recovery of succinic acid from fermentation broth." *Biotechnol Lett* 32: 331-339.

Knag, Y., Durfeem T., Glasner, J. D., Qiu, Y., Frisch, D., Winterberg, K. M., Blattner, F. R. "Systematic mutagenesis of the *Escherichia coli* genome." *J Bacteriol* 186: 4921-4930.

Kolisnychenko, V., Plunkett III, G., Herrigni, C. D., Feher, T., Posfai, J., Blattner, F. R., Posfai, G. "Engineering a reduced *Escherichia coli* genome." *Genome Res* 12: 640-647.

Lee, S. J., Lee, D-Y., Kim, T. Y., Kim, B. H., Lee J., Lee, S. Y. "Metabolilc Engineering of *Escherichia coli* for enhanced production of succinic acid, based on genome comparison and in silico gene knockout stimulation." *App Environ Microbiol* 71: 7880-7887.

Lee, S. Y., Lee, D. Y., Kim, T. Y. "Systems biotechnology for strain improvement." *Trends Biotech* 23: 349-358.

Lee, S. Y., Kim, J. M., Lee, J. W., Kim, T. Y., Jang, Y. S. "From genome sequence to integrated bioprocess for succinic acid production by *Mannheimia succiniproducens*." *App Microbiol Biotechnol* 79:11-22;

Lu, S., Eiteman, M. A., Altman, E. "pH and base counterion affect succinate production in dual-phase *Escherichia coli* fermentations." *J Ind Microbiol Biotechnol* 36:1101-1109.

Martinez, A., Grabar, T. B., Shanmugam, K. T., Yomano, L. P., York, S. W., Ingram, L. O. "Low salt medium for lactate and ethanol production by recombinant *Escherichia coli*." *Biotechnol Lett* 29:397-404.

Millard, C. S., Chao, Y-P., Liao, J. C. Donnelly, M. I. (1996) "Enhanced production of succinic acid by overexpression of phosphoenolpyruvate carboxyalse in *Escherichia coli*." *App Environ Microbiol* 62: 1808-1810.

Pernestig, A. K., Geogellis, D., Romeo, T., Suzuki, K., Tomenius, H., Normakr, S., Melefors, O. (2003) "The *Escherichia coli* BarA-UvrY two component system is needed for efficient switching between glycolytic and gluconeogenic carbon sources." *J Bacteriol* 185:843-853.

Ponce, E., Flores, N., Martinez, A., Valle, F., Bolivar, F. (1995) "Cloning of the two pyruvate kinase isoenzymes structural genes from *Escherichia coli*: the relative roles of these enzymes in pyruvate biosynthesis." *J Bacteriol* 177: 5719-5722.

Posfai, G., Plunket III, G., Feher, T., Frisch, D., Keil, G. M., Umenhoffer, K., Kolisnychenko, V., Stahl, B., Sharma, S., de Srruda, M., Burland, V., Harcum, S. W., Blattner, F. R. (2006) "Emergent properties of reduced-genome *Escherichia coli*." *Science* 312: 1044-1046.

Saier, M. H. Jr., and Ramseier, T. M. (1996) "The catabolite repressor/activator (Cra) protein of enteric bacteria." *J Bacteriol* 178: 3411-3417.

Sanchez A M, Bennett G N, San K Y (2005) "Novel pathway engineering design of the anaerobic central metabolic pathway in *Escherichia coli* to increase succinate yield and productivity." *Metab Eng* 7:229-239.

Siebold, C., Garcia-Alles, L. F., Erni, B., Baumann, U. (2003) "A mechanism of covalent substrate binding in the x-ray structure of subunit K of the *Escherichia coli* dihydroxy-acetone kinase." *Proc Natl Aca Sci USA* 100:8188-8192.

Silhavy, T., Berman, M., Enquist, L. (1984) "Experiments With Gene Fusions." Cold Spring Harbor Laboratory Press, Cold Spring Harbor, N.Y., pp 107-112

Subedi, K. P., Kim, I., Kim, J., Min, B., Park, C. (2007) "Role of gldA in dihydroxyacetone and methylglyoxal metabolism of *Escherichia coli* K12. *FEMS Microbiol Lett* 279: 180-187.

Suzuki, K., Wang, X., Weilbacher, T., Pernestig, A. K., Melefors, O., Georgellis, D., Babitzke, P., Romeo, T. (2002) "Regulatory circuitary of the CsrA/CsrB and BarA/UvrY systems of *Escherichia coli*." *J Bacteriol* 184:5130-5140.

Sivagamisundaram, C., Wooff, E., Coldham, N. G., Sritharan, M., Hewinson, R. G., Gordon, S. V., Wheeler, P. R. (2009) "Global effects of inactivation of the pyruvate kinase gene in the *Mycobacterium tuberculosis* complex." *J Bacteteriol* 191:7545-7553.

Truniger, V., Boos, W. (1994) "Mapping and cloning of gldA, the structural gene of the *Escherichia coli* glycerol dehydrogenase." *J Bacteriol* 176: 1796-1800.

Vemuri, G. N., Eiteman, M. A., Altman, E. (2002) "Effects of growth mode and pyruvate carboxylase on succinic acid production by metabolically engineered strains of *Escherichia coli.*" *App Environ Microbiol* 68: 1715-1727.

Wang, Q., Chen, X., Yang, Y., Zhao, X. (2006) Genome-scale in silico aided metabolic analysis and flux comparisons of *Escherichia coli* to improve succinate production." *App Microbiol Biotechnol.* 2006 73: 887-894.

Weickert, M. J., Adhya, S. (1993) "Control of transcription of Gal Repressor and isorepressor genes in *Escherichia coli.*" *J Bacteriol* 175: 251-258.

Zhang, X., Jantama, K., Moore, J. C., Jarboe, L. R., Shanmugam, K. T., Ingram, L. O. (2009a) "Metaboli evolution of energy-conserving pathways for succinate production in *Escherichia coli.*" *Proc Natl Acad Sci USA* 106: 20180-20185.

Zhang, X., Jantama, K., Shanmugam, K. T., Ingram, L. O. (2009b) "Re-engineering *Escherichia coli* for succinate production in mineral salts medium." *App Environ Microbiol* 75: 7807-7813.

What is claimed is:

1. A non-naturally occurring microorganism comprising an increased level of phosphoenol pyruvate carboxykinase enzyme activity encoded by an endogenous pck gene when compared to phosphoenol pyruvate carboxykinase enzyme activity in its naturally occurring wild type counterpart of said microorganism and a mutation in a pykA gene or homolog thereof causing a reduced level of pyruvate kinase enzyme activity wherein said increased level of phosphoenol pyruvate carboxykinase enzyme activity results from a mutation that increases the activity of phosphoenol pyruvate carboxykinase enzyme.

2. The non-naturally occurring microorganism of claim 1, wherein the increased level of phosphoenol pyruvate carboxykinase enzyme activity encoded by an endogenous pck gene when compared to phosphoenol pyruvate carboxykinase activity in its naturally occurring wild type counterpart of said microorganism results either from a mutation in promoter region of the endogenous pck gene or from genetic manipulation of at least one regulatory element that is known to interact with said promoter region of the endogenous pck gene.

3. The non-naturally occurring microorganism of claim 1, further comprising at least one genetic modification that decreases functioning of a phosphoenol pyruvate-dependent phosphotransferase system.

4. The non-naturally occurring microorganism of claim 1, further comprising:
  (a) at least one genetic modification that decreases functioning of a phosphoenol pyruvate-dependent phosphotransferase system; and
  (b) at least one genetic modification that increases activity of a non-phosphotransferase system sugar transporter.

5. The non-naturally occurring microorganism of claim 4, wherein said non-phosphotransferase system sugar transporter is a galactose permease.

6. The non-naturally occurring microorganism of claim 5, wherein the increase in the activity of said galactose permease is achieved by increasing copy number of a galP gene coding for said galactose permease.

7. The non-naturally occurring microorganism of claim 5, wherein the increase in the activity of said galactose permease is achieved by relieving negative control of a repressor of said galP gene through at least one mutation.

8. The non-naturally occurring microorganism of claim 7, wherein said repressor of said galactose permease is encoded by a galS or a galR gene.

9. The non-naturally occurring microorganism of claim 1, further comprising a mutation that decreases the functioning of at least one of the genes involved in a fermentative pathway selected from a group consisting of lactate dehydrogenase A, pyruvate-formate lyase, alcohol dehydrogenase E, phosphotrans-acetylase, acetate kinase A and pyruvate oxidase B.

10. The non-naturally occurring microorganism of claim 1, further comprising a mutation in a malate dehydrogenase gene associated with the operation of tricarboxylic acid cycle wherein said mutation increases malate dehydrogenase enzyme activity.

11. The non-naturally occurring microorganism of claim 1, further comprising a mutation in a rpoA gene set forth in SEQ ID NO: 4 encoding for alpha subunit of RNA polymerase wherein said mutation is a point mutation replacing a cytosine residue at nucleotide position 956 of said rpoA gene with a thymine residue leading to the replacement of a proline residue at amino acid position 322 of said alpha subunit of RNA polymerase with a leucine residue.

12. The non-naturally occurring microorganism of claim 1 further comprising a mutation in a rpoC gene set forth in SEQ ID NO: 5 encoding for a subunit of RNA polymerase wherein said mutation is a point mutation replacing a guanine residue at nucleotide position 2241 of said rpoC gene with an adenine residue leading to the replacement of a methionine residue at amino acid position 747 of said subunit of RNA polymerase with an isoleucine residue.

13. The non-naturally occurring microorganism of claim 1, further comprising a deletion in the chromosomal DNA of said microorganism wherein said deletion removes the ydcC, ydcD, ydcE, and ydcF genes.

14. The non-naturally occurring microorganism of claim 1, further comprising a mutation in ftsI gene set forth in SEQ ID NO: 8 coding for a protein involved in cell wall synthesis and cell separation wherein said mutation replacing a cytosine residue at nucleotide position 619 of said ftsI gene with a thymine residue leading to the replacement of an arginine residue at amino acid position 207 of said protein involved in cell wall synthesis and cell separation with a cysteine residue.

15. The non-naturally occurring microorganism of claim 1, further comprising a mutation in a gldA gene set forth in SEQ ID NO: 6 coding for a glycerol dehydrogenase enzyme, wherein said mutation is a frame shift mutation causing a decrease in activity of said glycerol dehydrogenase enzyme.

16. The non-naturally occurring microorganism of claim 1, further comprising a mutation in a dhaM gene set forth in SEQ ID NO: 7 encoding a subunit of a phosphotransferase-dependent dihydroxyacetone kinase enzyme, wherein said mutation is a frame shift mutation causing a decrease in the activity of said phospotransferase-dependent dihydroxyacetone kinase enzyme.

17. A method of producing succinic acid comprising:
  a. culturing the microorganism of any of claim 1 through claim 16;
  b. providing a carbon source;
  c. allowing said microorganism to metabolize said carbon source; and
  d. optionally, isolating succinic acid.

* * * * *